(12) United States Patent
von Oepen et al.

(10) Patent No.: US 8,100,860 B2
(45) Date of Patent: Jan. 24, 2012

(54) DEVICE AND METHOD FOR TREATING VULNERABLE PLAQUE

(75) Inventors: Randolf von Oepen, Los Altos Hills, CA (US); Kelly J. McCrystle, Menlo Park, CA (US); Richard R. Newhauser, Redwood City, CA (US); Travis R. Yribarren, Coarsegold, CA (US)

(73) Assignee: Abbott Laboratories, Abbott Park, IL (US)

( * ) Notice: Subject to any disclaimer, the term of this patent is extended or adjusted under 35 U.S.C. 154(b) by 286 days.

(21) Appl. No.: 12/328,731

(22) Filed: Dec. 4, 2008

(65) Prior Publication Data

US 2009/0254051 A1 Oct. 8, 2009

Related U.S. Application Data

(60) Provisional application No. 60/992,983, filed on Dec. 6, 2007.

(51) Int. Cl.
- *A61M 5/178* (2006.01)
- *A61M 31/00* (2006.01)
- *A61M 37/00* (2006.01)
- *A61M 25/00* (2006.01)

(52) U.S. Cl. ............... 604/164.12; 604/95.04; 604/523

(58) Field of Classification Search ............ 604/95.01, 604/95.04, 164.01, 164.12, 523; 623/1.1
See application file for complete search history.

(56) References Cited

U.S. PATENT DOCUMENTS

| | | | |
|---|---|---|---|
| 3,119,392 A * | 1/1964 | Zeiss et al. | 606/127 |
| 4,643,720 A * | 2/1987 | Lanciano | 604/95.04 |
| 4,762,130 A | 8/1988 | Fogarty et al. | |
| 5,041,085 A * | 8/1991 | Osborne et al. | 604/541 |
| 5,415,634 A | 5/1995 | Glynn et al. | |
| 5,464,395 A | 11/1995 | Faxon et al. | |
| 5,599,294 A | 2/1997 | Edwards et al. | |
| 5,919,163 A | 7/1999 | Glickman | |
| 6,030,362 A | 2/2000 | Boussignac et al. | |
| 6,450,988 B1 | 9/2002 | Bradshaw | |
| 6,458,098 B1 | 10/2002 | Kanesaka | |

(Continued)

FOREIGN PATENT DOCUMENTS

DE 102006003181 7/2007

(Continued)

OTHER PUBLICATIONS

U.S. Appl. No. 60/992,983, filed Dec. 6, 2007, von Oepen.

(Continued)

*Primary Examiner* — Nicholas Lucchesi
*Assistant Examiner* — Nathan R Price
(74) *Attorney, Agent, or Firm* — Workman Nydegger; Ron Devore

(57) ABSTRACT

A device and method is provided for localized agent delivery through a coronary vessel. In one configuration, the device includes an elongated member having a first and second end with a tip and an aperture positioned near the second end. An injection lumen places the first end of the elongated member in fluid communication with the aperture, permitting fluids such as contrast agent or therapeutic agents to be delivered therebetween. In an exemplary method, the device is tracked through a bend in the coronary anatomy, forcing the tip of the device toward the greater curve and through the vessel wall. The aperture may advanced to the desired location and agents may be delivered through the device into target tissue or space. Other configurations and embodiments of the device and method are presented.

17 Claims, 14 Drawing Sheets

U.S. PATENT DOCUMENTS

| | | |
|---|---|---|
| 6,508,789 B1 * | 1/2003 | Sinnott et al. ............ 604/164.02 |
| 6,554,801 B1 | 4/2003 | Steward et al. |
| 6,605,061 B2 * | 8/2003 | VanTassel et al. ....... 604/164.01 |
| 6,623,449 B2 * | 9/2003 | Paskar ...................... 604/95.04 |
| 7,273,469 B1 | 9/2007 | Chan et al. |
| 7,824,367 B2 * | 11/2010 | Accisano et al. .......... 604/95.04 |
| 2002/0072706 A1 | 6/2002 | Hiblar et al. |
| 2004/0118415 A1 | 6/2004 | Hall et al. |
| 2005/0070844 A1 * | 3/2005 | Chow et al. ................ 604/95.04 |
| 2005/0203462 A1 | 9/2005 | Katoh et al. |
| 2006/0015085 A1 * | 1/2006 | Bates .......................... 604/508 |
| 2009/0204068 A1 | 8/2009 | Nguyen et al. |
| 2010/0145264 A1 | 6/2010 | Min et al. |

FOREIGN PATENT DOCUMENTS

| | | |
|---|---|---|
| EP | 0810004 | 12/1997 |
| WO | WO 92/10142 | 6/1992 |
| WO | WO 94/04220 | 3/1994 |
| WO | WO 95/26776 | 10/1995 |
| WO | WO 2009/076215 | 6/2009 |
| WO | WO 2009/076224 | 6/2009 |

OTHER PUBLICATIONS

U.S. Appl. No. 12/328,054, filed Oct. 14, 2010, Office Action.
U.S. Appl. No. 12/328,390, filed Apr. 15, 2010, Office Action.
U.S. Appl. No. 12/328,390, filed Jun. 24, 2010, Office Action.
U.S. Appl. No. 12/328,390, filed Jan. 21, 2011, Office Action.

* cited by examiner

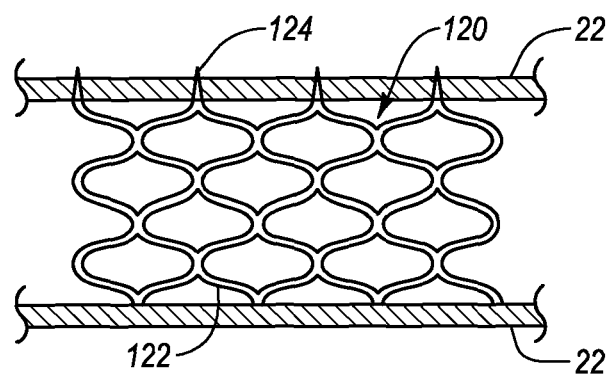
Fig. 29
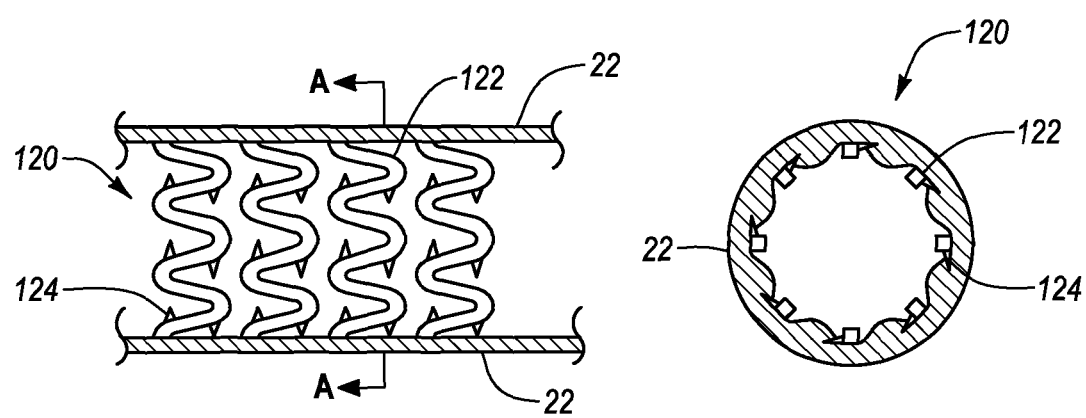
Fig. 30
Fig. 31

DEVICE AND METHOD FOR TREATING VULNERABLE PLAQUE

CROSS-REFERENCE TO RELATED APPLICATIONS

The present application claims priority to U.S. Ser. No. 60/992,983, filed on Dec. 6, 2007 entitled DEVICE AND METHOD FOR TREATING VULNERABLE PLAQUE, the entirety of which is hereby incorporated by reference.

BACKGROUND OF THE DISCLOSURE

1. The Field of the Invention

This invention, in one configuration, relates generally to the treatment of coronary disease, and more particularly, to the localized delivery of beneficial agents. In one configuration, the invention may be used for the treatment of vulnerable plaque.

2. The Relevant Technology

Coronary heart disease is generally thought to be caused by the narrowing of coronary arteries by atherosclerosis, the buildup of fatty deposits in the lining of the arteries. The process that may lead to atherosclerosis begins with the accumulation of excess fats and cholesterol in the blood. These substances infiltrate the lining of arteries, gradually increasing in size to form deposits commonly referred to as plaque or atherosclerotic occlusions. Plaques may narrow the arterial lumen and impede blood flow. Blood cells may collect around the plaque, eventually creating a blood clot that may block the artery completely.

The phenomenon of "vulnerable plaque" has created new challenges in recent years for the treatment of heart disease. Unlike occlusive plaques that impede blood flow, vulnerable plaque develops within the arterial walls, but it often does so without substantially narrowing the arterial lumen. Therefore, early symptoms of disease may not be present. As such, conventional methods for detecting heart disease, such as an angiogram, may not detect vulnerable plaque growth in the arterial wall. After death, an autopsy may reveal the plaque congested in arterial walls that could not have been seen otherwise with currently available medical technology.

The intrinsic histological features that may characterize a vulnerable plaque may include increased lipid content, increased macrophage, foam cell and T lymphocyte content, and reduced collagen and smooth muscle cell (SMC) content. This fibroatheroma type of vulnerable plaque is often referred to as "soft", having a large lipid pool of lipoproteins surrounded by a fibrous cap. The fibrous cap contains mostly collagen, whose reduced concentration combined with macrophage derived enzyme degradations can cause the fibrous cap of these lesions to rupture under unpredictable circumstances. When ruptured, the lipid core contents, thought to include tissue factor, contact the arterial bloodstream, causing a blood clot to form that can completely block the artery resulting in an acute coronary syndrome (ACS) event. This type of atherosclerosis is coined "vulnerable" because of the unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of simple movements, such as getting out of bed in the morning, in addition to in vivo forces related to blood flow and the beating of the heart. It is thought that plaque vulnerability in fibroatheroma types is determined primarily by factors which may include: (1) size and consistency of the lipid core; (2) thickness of the fibrous cap covering the lipid core; and (3) inflammation and repair within the fibrous cap.

FIG. 1A illustrates a partial cross section of an artery having a narrowed arterial lumen caused by the presence of occlusive atherosclerosis. Plaque may accumulate to impede and reduce blood flow through the arterial lumen and thus may often cause symptoms (e.g., angina pectoris). The arrows indicate the direction of blood flow through the arterial lumen. FIG. 1B illustrates an occlusive atherosclerosis within an arterial lumen resulting in significant reduction in lumen patency. This type of atherosclerosis can easily be detected through current diagnostic methods such as an angiogram. FIG. 1B also illustrates, downstream from the occlusive atherosclerosis, a fibroatheroma type of vulnerable plaque. The vulnerable plaque, with a lipid core, develops mostly within the arterial wall with minimal occlusive effects such that it is not easily detected by current diagnostic methods. This is partially due to a phenomenon known as "positive remodeling", which allows the vessel to respond to the presence of disease. The fibroatheroma vulnerable plaque has grown into the positively remodeled arterial wall so that vessel occlusion has not been manifested. A fibrous cap surrounds the vulnerable plaque.

FIGS. 2A-2C illustrate a cross-sectional view of the accumulation of vulnerable plaque in the arterial wall. FIG. 2A illustrates an arterial wall that is not affected by atherosclerosis. The normal arterial wall consists of an intima layer, a media layer, and an adventitia layer. The intima is in direct contact with the blood flow within the arterial lumen. The intima consists mainly of a monolayer of endothelial cells. The media consists mostly of smooth muscle cells and extracellular matrix proteins. The outermost layer of the arterial wall, the adventitia, is primarily collagenous and contains nerves, blood vessels, and lymph vessels. FIG. 2B illustrates the large presence of a fibroatheroma type vulnerable plaque surrounded by a fibrous cap within the arterial wall. The vulnerable plaque consists mainly of a large lipid core. The fibrous cap layer shields the lumen of the artery from the thrombogenic components in the core. FIG. 2C illustrates an occlusive thrombosis event resulting from the rupturing of the fibrous cap. Thrombogenic components in the vulnerable plaque contact luminal blood and cause the thrombotic event.

Autopsy studies and other evidence strongly suggest that the presence of a current acute coronary syndrome (ACS) event and/or existing thrombus at certain plaque sites may correlate to predicting a future ACS event in a given patient. The latter indicates the likelihood of a prior thrombotic event (e.g., fibroatheroma rupture) after which the plaque was able to heal itself, or complete occlusion of the vessel was somehow prevented. Autopsy studies also indicate that it is reasonable to expect that at least one vulnerable plaque could exist in the majority of catheterization laboratory patients being treated for arterial blockage from visible occlusive atherosclerosis. Many of the patients at highest risk, therefore, for future ACS events may already be receiving interventional treatment, even though current methods to diagnose occlusive plaques (i.e., non-vulnerable type plaque) may not be effective for enabling therapy for vulnerable plaque. Furthermore, treating both the occlusive plaques and the vulnerable plaque in one procedure might be beneficial and desirable compared to separate treatments. This would provide a greater convenience to the patient and for the physician.

One method for the treatment or prevention of disease that has been suggested is the extravascular administration of anti-microtubule agents such as paclitaxel. This method has specifically focused on the administration of the agents either through the chest wall or external surface of the pericardial sac, such as in open chest procedures. The pericardial sac is the anatomical space between the two layers of the pericardium. Additionally, it has been suggested that the pericardial sac can be accessed through the atrial or ventricular walls of the heart using catheter guided needles. The procedures described have a major disadvantage in light of the previous discussion since they do not readily lend themselves to treating occlusive plaques and vulnerable plaque disease in the same procedure. Additionally, the techniques used to administer the agents may be significantly different from common interventional cardiology techniques such as PTCA, therefore requiring significant physician training. Finally, the techniques may be time consuming, making them less desirable options for treating coronary disease.

Another method of treating coronary disease through the delivery of a therapeutic substance includes the use of a catheter-based device incorporating a needle whereby the substance can be delivered to the treatment site, such as a vessel wall or lesion therein. While this disclosure may be more similar to conventional interventional techniques than the method previously discussed, it may have the disadvantage of only providing localized delivery of the substance within the heart. In the case of vulnerable plaque, the disease may be profuse and difficult to identify throughout the entire coronary vascular tree. Therefore, the localized nature of this method may result in a higher potential of ineffective treatment.

BRIEF SUMMARY OF THE DISCLOSURE

Configurations of the disclosed inventions can be aimed at providing a medical device that can access an extravascular space through the wall of a coronary vessel. The device may subsequently administer a therapeutic agent to treat and/or prevent coronary diseases such as vulnerable plaque. Configurations of the disclosed inventions may effectively deliver therapeutic agents to an extravascular space, such as the pericardial space. Additionally, the treatment may provide for a systemic type of treatment that may improve the chance of effectively treating difficult to identify vulnerable plaques.

To achieve at least one of these purposes and/or advantages, and in accordance with the present disclosure, a medical device is provided for localized agent delivery through the wall of a coronary vessel. In a configuration, an elongated member is provided having a proximal and distal end. An access tip can be disposed on the elongated member near the distal end. The elongated member may include an internal lumen that places the proximal and distal end of the elongated member in fluid communication. In one configuration, the access tip is configured to permit access to the extravascular space by penetrating the coronary vessel wall, for example. In further accordance with the exemplary configuration, an aperture may be disposed adjacent to the access tip being in fluid communication with the internal lumen of the elongated member, thereby permitting the delivery of a therapeutic agent through the internal lumen into the extravascular space.

In an alternative configuration, the access tip may have a variety of configurations that are suitable for localized agent delivery through a coronary vessel wall. For example, the access tip may have a cross-sectional profile that is circular or non-circular, and/or may be tapered or comprise edges to help penetrate and spread the coronary vessel wall, thereby easing passage of the elongated member.

In still another alternative configuration, the medical device may include a sealing element, such as a sleeve configured and dimensioned to mate with the medical device surface, the element being moveable between a first and second position, whereby the aperture is sealed when the sleeve is in one position, but not when the sleeve is in the other position.

In an alternative configuration, a medical device is provided that further includes an injection member disposed within the internal lumen of the elongated member. The injection member includes a proximal and distal end with an injection lumen therebetween. The injection lumen permits the delivery of a therapeutic agent through the injection member. The injection member can be moved between a first position, in which the distal end is disposed within the internal lumen of the elongated member, and a second position, in which the distal end is passed through the aperture of the elongated member.

In a further aspect of the alternative configuration, the medical device may further include a biasing member disposed on the elongated member near the aperture. The biasing member may be an arcuate band, for example. The biasing member may urge the elongated member toward a non-linear configuration, causing the elongated member to rotationally orient in a specific manner when passed through a curved path, such as through a coronary vessel bend. The natural orientation of the elongated member can place the aperture near the outer curve of the bend, thereby ensuring that the injection member is directed toward the extravascular space when it is moved from the first position to the second position.

In yet another alternative configuration, the medical device may further include multiple apertures disposed adjacent to each other within the elongated member. The apertures may result in a decrease in cross-sectional area of the elongated member, increasing the localized flexibility of the elongated member. By doing so, the elongated member may tend toward a rotational orientation that may bias one of the apertures toward the outer curve when it is tracked through a coronary vessel bend. This can also result in an increase in the area of at least one aperture, since the aperture will be located in a section of the elongated member that is under tension from bending, thereby easing the passage of the injection member when it is moved from the first position to the second position.

In yet another configuration, an actuation cord may be associated with the second end of the elongated member, such that when in a relaxed position, the elongated member is configured in a natural position, but when a tensile load is applied to the actuation cord, the elongated member is urged toward a non-linear configuration over a portion of its length. This non-linear configuration may bias the rotational orientation of the elongated member and can be used to ease the direction of the injection member toward the extravascular space, as described above.

In an alternative configuration in accordance with the present disclosure, a medical device for localized agent delivery is provided that includes multiple injection members having injection lumens for delivering fluids such as contrast solution or therapeutic agents therethrough. The injection members are disposed within the internal lumens of an elongated member, and are moveable from a first position to a second position. The injection members may have a pre-set curved shape that allows them to follow a curvilinear path as they pass from one position to the other. For example, the exposed injection members may curve outwardly in a substantially longitudinal direction. Alternatively, the injection members may follow a curved path outward in a substantially transverse direction.

In yet another alternative configuration, a medical device for localized agent delivery is provided that includes an elongated member having a first and second end placed in fluid communication by an internal lumen disposed therebetween. The medical device may further include a detachable access tip initially placed in communication with the internal lumen. The detachable tip may be configured to ease insertion through the coronary vessel wall and/or to resist retraction into the coronary vessel after insertion. As a result, retraction of the elongated lumen after insertion of the detachable tip through the coronary vessel wall may create a dislodging force that may disassociate the detachable tip from the elongated member.

In a further aspect of the configuration, the detachable access tip further includes a therapeutic substance for delivery into the extravascular space. It is further contemplated that the detachable tip may be formed from a bioabsorbable material.

In another configuration, a device for delivering a therapeutic agent into the extravascular space through a coronary vessel wall is provided. The device includes an elongated member having a first and second end with an internal lumen disposed therebetween. The device may include an expandable structure such as a balloon component disposed near the second end of the elongated member. The device may include an aperture adjacent the surface of the expandable structure, the aperture being in fluid communication with the first end of the elongated member. The device may allow a therapeutic agent to be delivered through the elongated member and/or to exit through the aperture at a sufficient velocity to cross through the coronary vessel wall into the extravascular space.

In yet another configuration, a stent device is provided that includes a series of strut elements arranged in an expandable structure. The strut elements may include at least one protrusion directed substantially in the radial direction. The stent can be expanded from a first low profile configuration toward a second high profile configuration by, for example, placing the stent on a balloon component of a balloon catheter prior to inflating the balloon and expanding the stent. When the stent structure is expanded, the protrusions may pass through the coronary vessel wall into the extravascular space. The protrusions may include a therapeutic agent, whereby when the protrusions enter the extravascular space, the therapeutic agent may be delivered.

It is to be understood that both the foregoing general description and the following detailed description are exemplary and are intended to provide further explanation of the disclosure claimed. The accompanying drawings, which are incorporated in and constitute part of this specification, are included to illustrate and provide a further understanding of the disclosure. Together with the description, the drawings serve to explain principles of the disclosure.

These and other objects and features of the present disclosure will become more fully apparent from the following description and appended claims, or may be learned by the practice of the disclosure as set forth hereinafter.

BRIEF DESCRIPTION OF THE DRAWINGS

To further clarify the above and other advantages and features of the present disclosure, a more particular description of the disclosure will be rendered by reference to specific configurations or embodiments thereof which are illustrated in the appended drawings. It is appreciated that these drawings depict only typical configurations or embodiments of the disclosure and are therefore not to be considered limiting of its scope. The disclosure will be described and explained with additional specificity and detail through the use of the accompanying drawings in which:

FIG. 29 is a side elevation view illustrating a stent device having protrusions in accordance with this disclosure;

FIG. 30 is a side elevation view illustrating a further configuration of a stent device having protrusions in accordance with this disclosure;

FIG. 31 is a cross-sectional view illustrating a further configuration of a stent device having protrusions in accordance with this disclosure, taken about line A-A of FIG. 30.

DETAILED DESCRIPTION

Figure 1A:
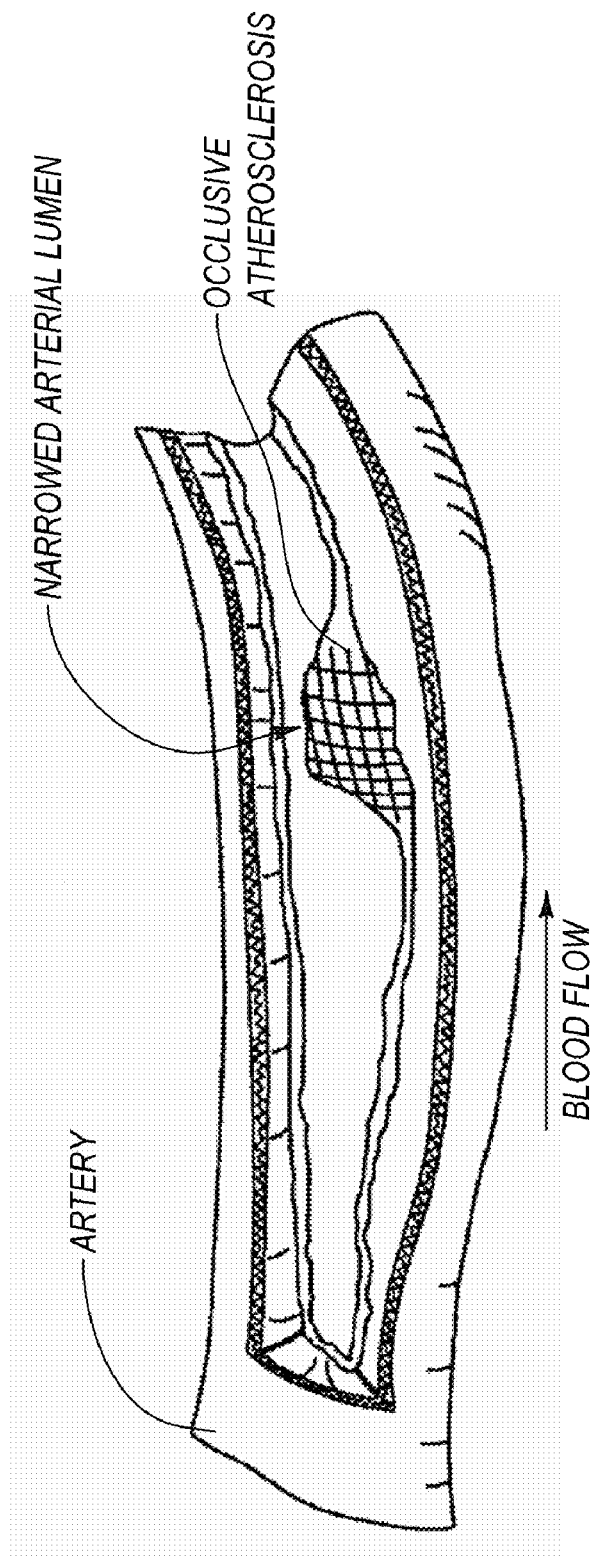
FIG. 1A shows a partial cross-section of an arterial lumen having occlusive atherosclerosis.

While the present disclosure will be described in detail with reference to a few specific configurations, the description is illustrative and is not to be construed as limiting the disclosure. Various modifications can be made to the illustrated configurations without departing from the spirit and scope of the invention as defined by the appended claims. It will be noted here that for a better understanding, like components have been designated by like reference numerals through the various accompanying figures.

Figure 1B:
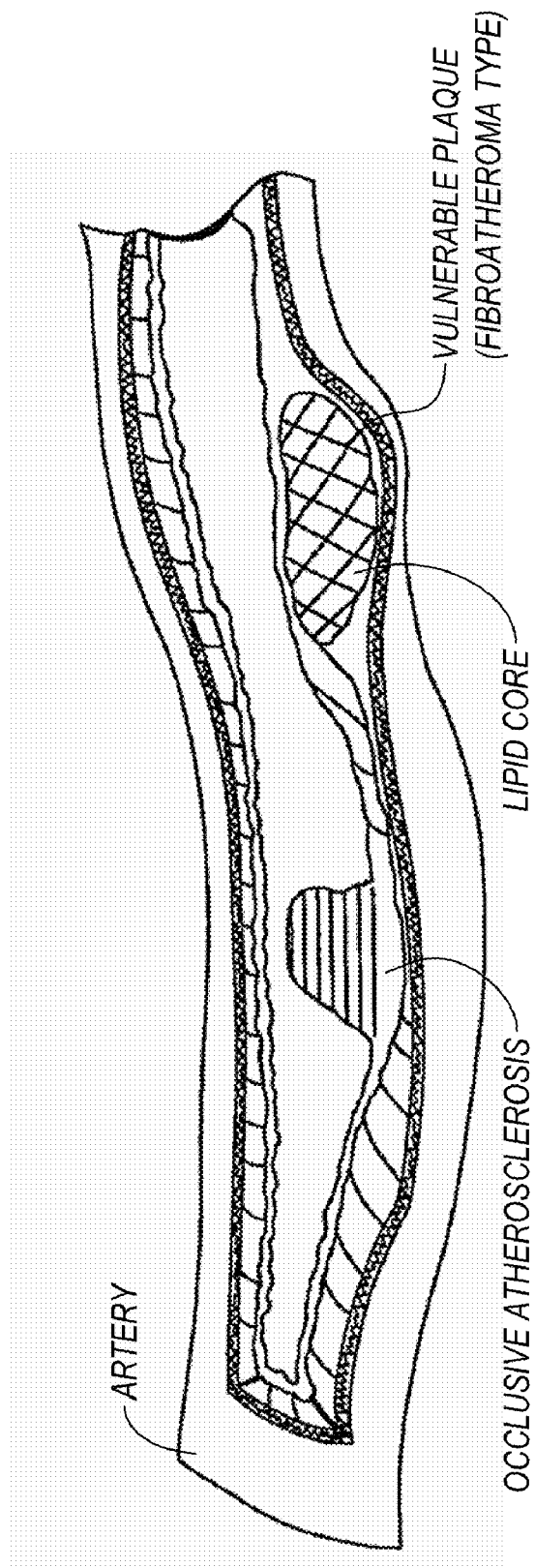
FIG. 1B shows a partial cross-section of an arterial lumen having occlusive atherosclerosis and vulnerable plaque.
Figure 2A:
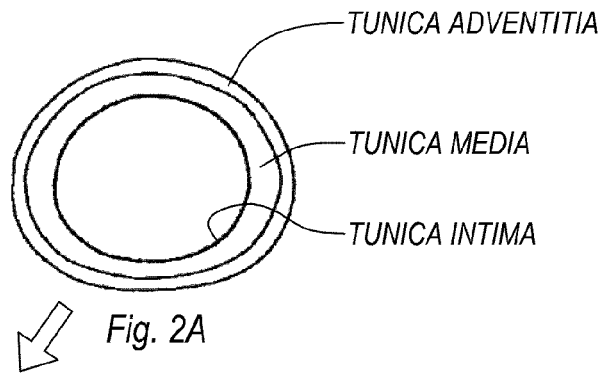
FIGS. 2A-2C show the vessel morphology and the rupturing of a vulnerable plaque.
Figure 2B:
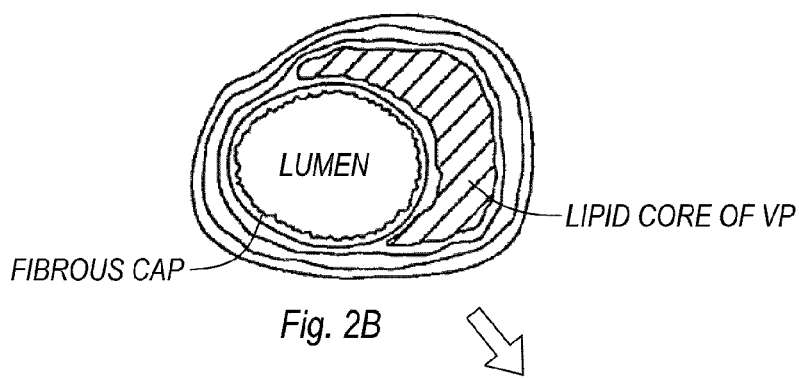
Figure 2C:
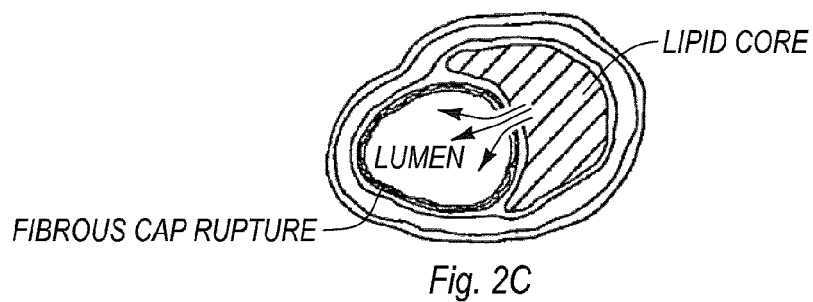
Figure 3:
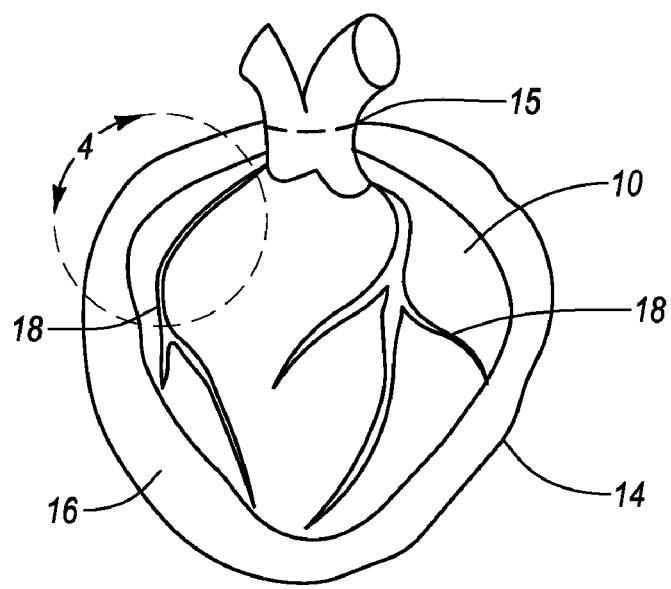
FIG. 3 illustrates the anatomy of the heart and pericardial sac.

Referring to FIG. 3, the coronary anatomy is shown to illustrate the exemplary anatomical structures associated with the invention description. The heart 10 is identified with related coronary arteries 18 disposed substantially on the outer surface of the heart 10. Surrounding the heart 10 is the pericardial sac 14. One function of the pericardial sac 14 is to provide a protective barrier around the heart 10 that prevents against infections. The pericardial sac 14 attaches to the aortic and pulmonary arteries in a superior location relative to the heart 10, shown as attachment location 15 in FIG. 1. It will be understood from viewing the anatomical illustration that the pericardial sac 14 and heart 10 define a extravascular space 16. This extravascular space 16 is normally filled with a fluid. Among other functions, the fluid acts as a lubricant between the heart 10 and the pericardial sac 14 as the heart 10 expands, contracts, and moves during normal operation. The heart 10 therefore provides a natural mixing action within the pericardial space 16. As a result, a fluid that is introduced locally within the pericardial space 16 will have a tendency to disperse evenly throughout the entire space.

Figure 4:
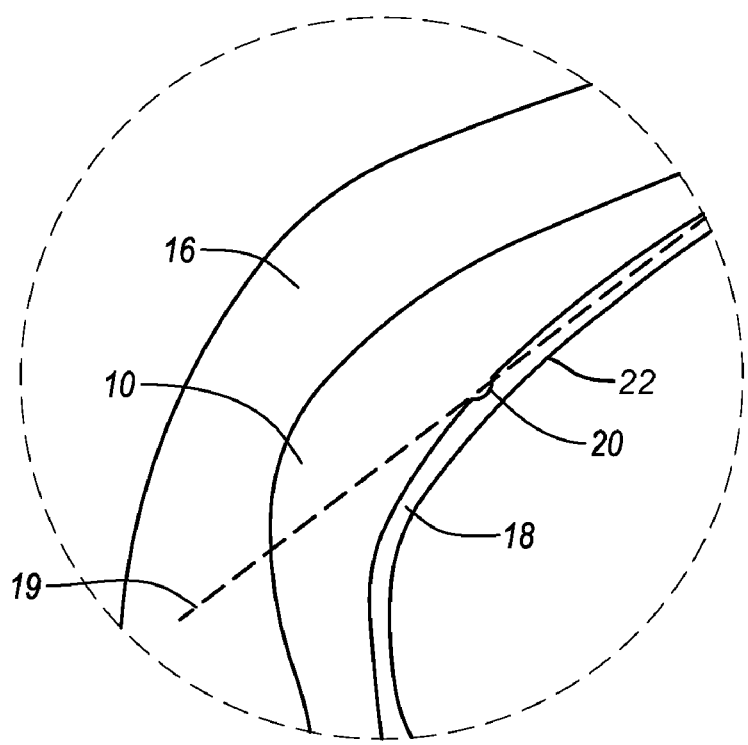
FIG. 4 illustrates a magnified view of a portion of the heart.

Referring now to FIG. 4, a portion of the outer heart surface is shown to further illustrate the anatomical structures that are relevant to this invention. The heart 10 is shown, and in this illustration, the right coronary artery 18 has been identified. The right coronary artery 18 is a coronary vessel defined by a coronary vessel wall 22. The right coronary artery 18 was chosen for this illustration because it normally includes a relatively sharp bend as it descends from the aorta and curves along the surface of the heart 10. When a catheter device is tracked through the coronary vessels in an antegrade direction, it has a tendency to follow tangential direction line 19, as shown in the figure. The device will cross through the coronary vessel wall 22 into the extravascular space 16 at an access site 20, unless there is sufficient resistance provided by the coronary vessel to retain the device and direct it along the curve of the vessel instead.

Figure 5:
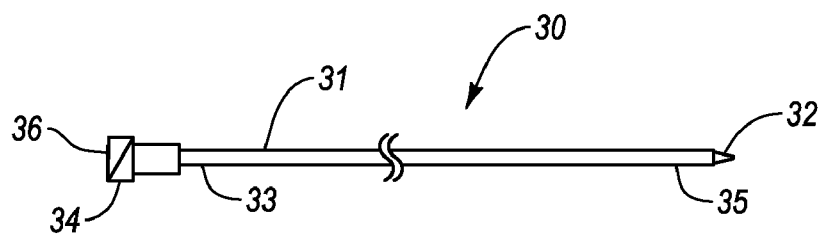
FIG. 5 is a side elevation view of one configuration of a device in accordance with this disclosure.

Referring now to FIG. 5, a device for locally delivering a beneficial or therapeutic agent (it shall be understood that these terms will be used interchangeably herein and have the same or similar meanings) is shown that may be used for accessing the extravascular space 16 of the coronary anatomy. The agent delivery device 30 includes an elongated member 31 with a proximal end 33 and a distal end 35. The elongated member 31 is generally configured and dimensioned to be capable of tracking through the cardiovascular system. Further still, the elongated member 31 includes an injection lumen formed therein (not shown) that places the proximal end 33 and the distal end 35 in fluid communication.

In one configuration, the elongated member 31 can be constructed from a flexible polymer tubing. Suitable polymers for this purpose include those typically used in catheter construction. For example, the polymer tubing may be formed from nylon, urethane, polyurethane, polyvinylchloride, polyester, PEEK, PTFE, PVDF, Kyner, polyimide, or polyethylene of various suitable densities. The elongated member 31 may be further supported by a coiled or braided wire structure over at least a portion of its length.

In further accordance with the presently described configuration, a luer fitting 34 can be associated with the proximal end 33 of the elongated member 31. The luer fitting 34 enables the attachment of an accessory device such as a syringe 77 (FIG. 23) or a fluid manifold to the agent delivery device 30, whereby agents and materials such as therapeutic agents or contrast agents can be delivered through the luer 34 and injection lumen 36 to the distal end 35.

Therapeutic agents useful in accordance with this disclosure may include a therapeutically effective amount of zotarolimus or derivatives, salts, prodrugs, or esters thereof. In further accordance with the present disclosure, the drugs or beneficial agents that can be delivered into the vessel wall include anti-proliferative and cytostatic drugs such as Everolimus, ABT-578, tacrolimus and pimecrolimus, angiopeptin, calcium channel blockers such as nifedipine, amlodipine, cilnidipine, lercanidipine, benidipine, trifluperazine, diltiazem and verapamil, fibroblast growth factor antagonists, fish oil (omega 3-fatty acid), histamine antagonists, lovastatin. In addition, topoisomerase inhibitors such as etoposide and topotecan, as well as antiestrogens such as tamoxifen can be used. Other beneficial agents that are useful in accordance with this disclosure include anti-inflammatory, antineoplastic, antiplatelet, anti-coagulant, anti-fibrin, antithrombotic, antimitotic, antibiotic, antiallergic and antioxidant compounds. It will be appreciated that still other types of drugs or beneficial agents may be delivered and taken up by a vessel wall by using the devices and methods described herein.

A method for delivering a substance into the extravascular space is provided in accordance with the present disclosure. The method may include several acts or steps performed in various orders, including the introduction of a device such as the one described above into the vascular system of a patient. For the purposes of understanding, it should be realized that the catheter might be tracked into a coronary vessel, including vessels that are arteries or veins. Although the device may access the extravascular space through the vessel wall at various locations, in one embodiment, the device accesses the extravascular space through a distal region of the coronary vessel. Achieving access in a distal anatomy may ensure that the distal end 35 of the device is within a region of the coronary vessel with relatively low flow velocities and may reduce the risk of significant blood loss in the inadvertent event of a vessel dissection. The access tip 32 may be advanced until it contacts and penetrates the vessel wall. This will happen, for example, when the device is tracked through a vessel of a given curvature.

After penetrating the coronary vessel, the device may be advanced far enough to ensure that the access tip 32 of the device is within the extravascular space. A therapeutic agent may then be injected through the injection lumen 36 of the device, into the extravascular space. The substance may disperse within the extravascular space by the natural mixing action of the heart 10 and the substance may be administered to the desired area(s) through this dispersion.

After delivering the substance, the device may be removed into the coronary vessel through the access site. Secondary acts or steps may be utilized to close the access site, if blood loss through the access site appears to be excessive as viewed under medical visualization technologies such as fluoroscopy. An example of a secondary act or step is the inflation of an angioplasty balloon within the access region to facilitate closure of the access site.

Figure 6:
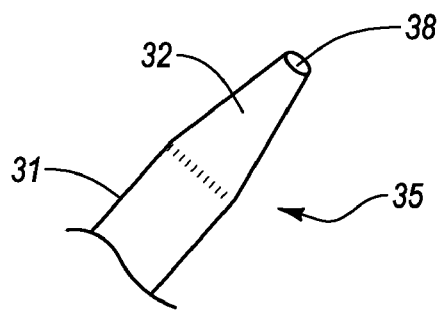
FIG. 6 is a perspective view of a distal portion of one configuration of a device in accordance with this disclosure.

Referring now to FIG. 6, a distal end 35 of the agent delivery device in accordance with the present disclosure is shown. An access tip 32 is shown associated with the distal end 35 of the elongated member 31. Aperture 38 is shown located adjacent to distal end 35 of the elongated member 31. The aperture 38 can be placed in fluid communication with the proximal end 33 of the elongated member 31 by the injection lumen 36.

According to the present configuration, the access tip 32 is configured such that the cross-sectional area of the access tip 32 adjacent to the distal end 35 of the elongated member 31 is less than the cross-sectional area near the opposite end of the access tip 32. This configuration enables the access tip 32 to penetrate the vessel wall at an access site 20. As the device is advanced further, the vessel wall may reversibly widen due to the increased cross-sectional area of the access tip 32. Since the vessel wall is elastic, it will typically recoil upon removal of the access tip 32 from the vessel wall. The cross-sectional area of access tip 32 may be substantially circular or have another geometrical cross-sectional shape such as an ellipse.

Figure 7:
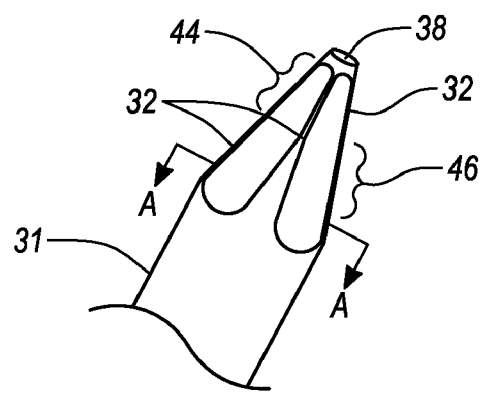
FIG. 7 is a perspective view of a distal portion of a further configuration of a device in accordance with this disclosure.

Referring now to FIG. 7, an alternative configuration of an access tip 32 is shown. The access tip 32 is shown associated with the distal end 35 of the elongated member 31. Aperture 38 is located at or near the distal end 35 of the elongated member 31. The aperture 38 can be placed in fluid communication with the proximal end 33 of the elongated member 31 by the injection lumen 36.

Figure 7A:
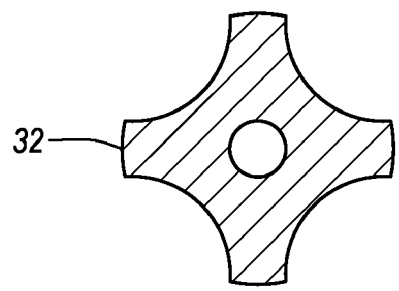
FIG. 7A is a cross-sectional view of an access tip of a further configuration of a device in accordance with this disclosure, taken about line A-A of FIG. 7.

The access tip 32 can be configured such that the cross-sectional area has substantially angular features, such as the cross-section shown in FIG. 7A. In this configuration, the access tip 32 includes edges spaced circumferentially from one another. These edges may further comprise varying edge sharpness. In further accordance with this configuration, and as illustrated in FIG. 7, the edge can be sharper at a distal sharp edge segment 44 than at a proximal blunt edge segment 46. Accordingly, the tip 32 can access the extravascular space through a coronary vessel wall 22 by creating a relatively small penetration compared to the cross-sectional area of the distended access site 20 once the device is advanced further.

In a further configuration, the aperture 38 may be positioned along a lateral surface of the access tip 32 or elongated member 31. In this case, the distal end 35 of the access tip 32 may be made to be more atraumatic by using a domed construction, for example. A configuration that is in accordance with this concept will now be explained in greater detail.

Figure 8:
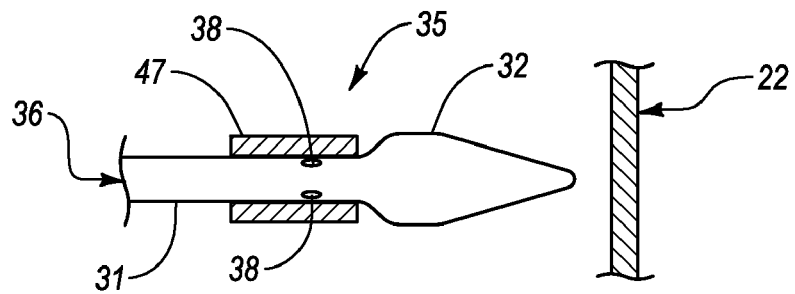
FIG. 8 is a side elevation view of a distal portion of a further configuration of a device in accordance with this disclosure, wherein a sealing component covers an exit port.

Referring to FIG. 8, a distal end 35 of an agent delivery device in accordance with a further configuration is shown. The device includes apertures 38 positioned in the lateral wall of the elongated member 31 near its distal end 35. An access tip 32 is shown having a domed distal end 35. A sleeve 47 may be sized and dimensioned to be disposed over the elongated member 31 and/or positioned in a first location, whereby the apertures 38 may be covered, preventing fluid from exiting from the injection lumen 36 of the device through the apertures 38 into the surrounding environment.

Figure 9:
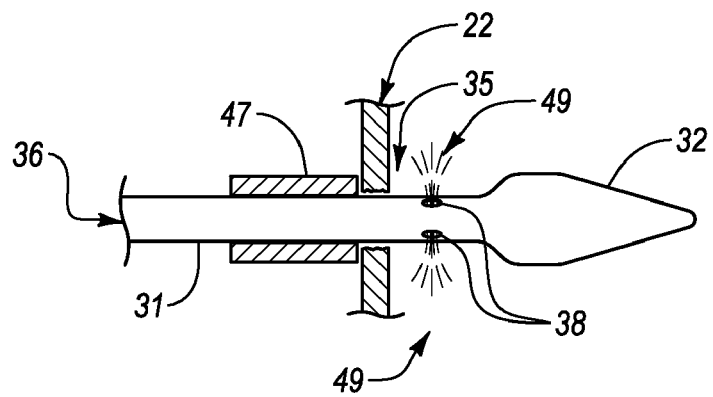
FIG. 9 is a side elevation view of a distal end of a further configuration of a device in accordance with this disclosure, wherein a sealing component does not cover an exit port.

Referring now to FIG. 9, the device is shown in a second orientation wherein the distal end 35 of the device has accessed the extravascular space through the vessel wall. During advancement of the device into the extravascular space, the vessel wall has moved the sleeve 47 to a second location that is proximal to the first location. This hereby may uncover the apertures 38 and/or may permit the delivery of an agent 49 through the injection lumen 36 into the surrounding extravascular space.

In a further configuration, the device may be configured such that a sleeve 47 is located distal to the apertures 38 when it is in a first position. In this configuration, delivery of an agent from the injection lumen 36 into the surrounding environment may be possible. The sleeve 47 is designed to remain within the first position unless a threshold force is applied to it. For example, the force applied by the vessel wall to the sleeve 47 as the device is advanced through the vessel wall into the extravascular space may be lower than the threshold force. By this same example, the force applied by the myocardium as the device is advanced through the vessel wall into the heart muscle may be greater than the threshold force. When the threshold force is exceeded, the sleeve 47 may move to a second location, wherein the sleeve 47 covers the apertures 38 and delivery of an agent from the injection lumen 36 into the surrounding environment is may be limited. Accordingly, a device is provided that may permit delivery of an agent into the extravascular space but may inhibit delivery of an agent if the myocardium is mistakenly accessed through the coronary vessel wall 22.

Figure 10:
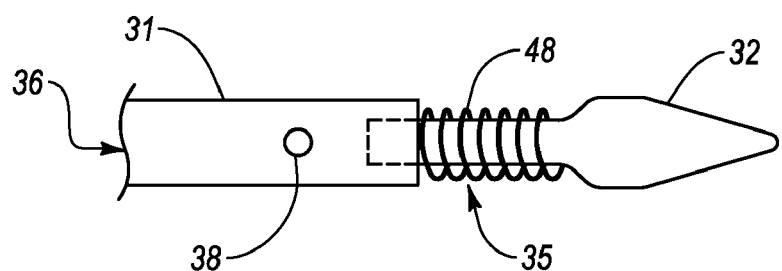
FIG. 10 is a side elevation view of a distal end of a further configuration of a device in accordance with this disclosure having a biasing element in association with the device tip.

Referring now to FIG. 10, a further configuration of a distal end 35 of an agent delivery device is shown. An elongated member 31 is provided, and further, an access tip 32 is shown at or near the distal end 35 of the elongated member 31, being in association with the elongated member 31. A biasing element 48 may be associated with both the elongated member 31 and the access tip 32. In accordance with this configuration, the biasing element 48 may be a compression spring that acts between the elongated member 31 and the access tip 32, thereby biasing the access tip 32 toward a distal first position. If a sufficient compressive load is placed on the access tip 32, it may cause compression of the biasing element 48, and may therefore move the access tip 32 toward a second position that is proximal relative to the first position.

In further accordance with the presently described configuration, an aperture may be located in the elongated member 31 proximal to the proximal end 33 of the access tip 32 when the access tip 32 is in the first position. Further, when the access tip 32 is moved to the second position, the aperture may be sealed by the access tip 32, thereby inhibiting delivery of an agent from an injection lumen 36 through the aperture into the surrounding environment.

Accordingly, the access tip 32 may be designed to remain within the first position unless a threshold force is applied to it. For example, the force applied by the vessel wall to the access tip 32 as the device is advanced through the vessel wall into the extravascular space may be lower than the threshold force. By this same example, the force applied by the myocardium as the device is advanced through the vessel wall into the heart muscle may be greater than the threshold force. When the threshold force is exceeded, the access tip 32 may move to the second position, wherein aperture 38 may be sealed and delivery of an agent from the injection lumen 36 into the extravascular space may be inhibited. Accordingly, a device may be provided that permits delivery of an agent into the extravascular space, but inhibits the delivery of an agent if the myocardium is mistakenly accessed through the coronary vessel wall 22.

A method for delivering a substance into the extravascular space is provided. The method may include several acts or steps performed in various orders performed in various orders including the introduction of a device, as embodied in the examples above, into the vascular system of a patient. For the purposes of understanding, it should be realized that the catheter may be tracked into a coronary vessel, including vessels that are arteries or veins. Although the device may be tracked to any point at which the extravascular space may be accessed through the vessel wall, it may be desirable to track the device to a distal region of the coronary vessel. This may ensure that the distal end 35 of the device is within a region of the coronary vessel with relatively low flow velocities and reduces the risk of significant blood loss if the vessel is inadvertently dissected. The access tip 32 of the device may be advanced until it contacts and/or penetrates the vessel wall. This may happen, for example, when the device is tracked through a vessel with a given curvature.

After penetrating the coronary vessel, the device may be advanced far enough to ensure that an aperture of the device is within the extravascular space. A substance such as a therapeutic agent may then be injected through an aperture of the device into the extravascular space. The substance may disperse within the extravascular space by the natural mixing action of the heart 10 and the substance may be administered to the desired areas through this dispersion.

After delivering the substance, the device may be removed into the coronary vessel entirely. Secondary acts or steps may be utilized to close the access site, if blood loss through the access site seems excessive. This determination may be made using standard medical visualization technologies, such as fluoroscopy. An example of a secondary act is the inflation of an angioplasty balloon within the access region to facilitate closure of the access site.

Figure 11:
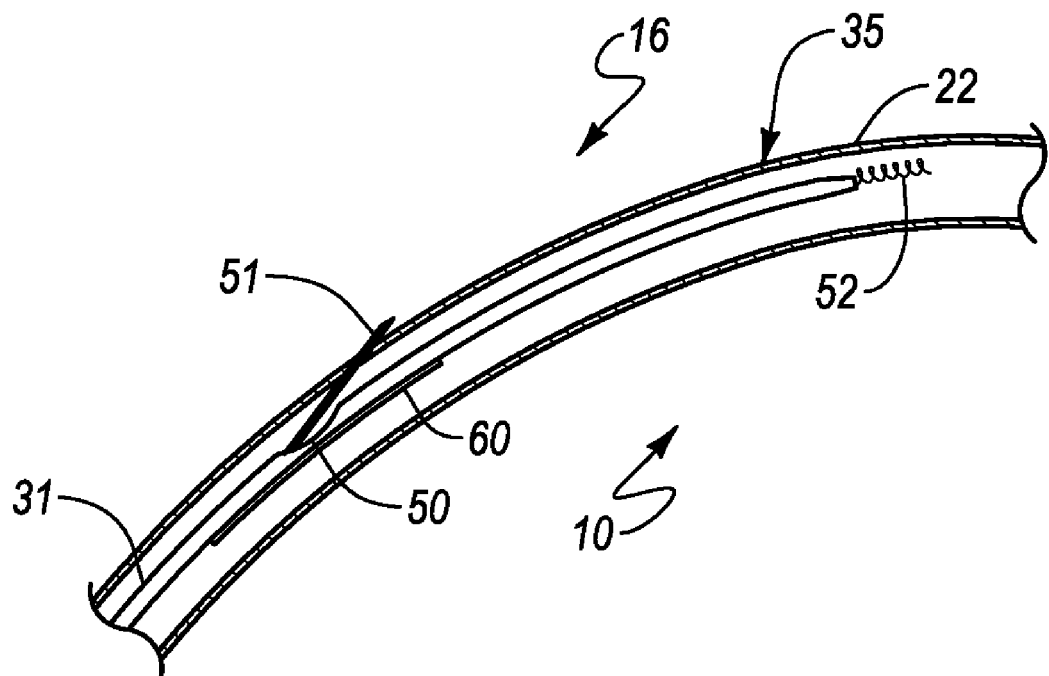
FIG. 11 is a perspective view illustrating a distal portion of a further configuration of a device in accordance with this disclosure disposed within a coronary vessel.

Referring now to FIG. 11, a distal portion of a further configuration of an agent delivery device is shown. In this configuration, the device includes an elongated member 31 having a proximal end and a distal end 35. A flexible tip 52 is disposed adjacent the distal end 35, and may be constructed in a coiled configuration. The flexible tip 52 may be atraumatic to the vessel wall 22, allowing the elongated member 31 to be tracked through a tortuous vessel anatomy. The device further includes an exit port 50 positioned in the elongated member 31 that places an internal lumen (not shown) disposed within the elongated member 31 in fluid communication with the surrounding environment. The internal lumen may be sized and dimensioned to receive an injection member 51. The injection member 51 has a proximal end and a distal end 35 and further includes an injection lumen that permits fluid communication between the proximal end and the distal end 35. An aperture (not shown) may be positioned at or near the distal end 35 of the injection member 51, placing the injection lumen in fluid communication with the surrounding environment.

Further, the injection member 51 may be movable within the internal lumen of the elongated member 31 and may be positioned in a first retracted position wherein the distal end 35 of the injection member 51 is disposed within the internal lumen of elongated member 31, or it may be positioned in a second extended position wherein the distal end 35 of the injection member 51 is not disposed within the internal lumen of elongated member 31.

In further accordance with this configuration, the device may include an arcuate member 60 that may be associated with the elongated member 31 in a location adjacent and opposite to the exit port 50. This arcuate member 60 may bias a portion of the elongated member 31 toward an arcuate configuration.

The arcuate member 60 may comprise a curved metal band, the metal being deformable, having a shape-memory, or both, for example. A plastic material may be used to form the arcuate member 60.

In a further configuration, the arcuate configuration of the device can be achieved by shaping the device body. This can be done, for example, by placing the device body in a curve and subsequently heating and cooling it as necessary to cause the body to reshape in an arcuate configuration.

It will be appreciated that when tracking the arcuate member 60 of the device through a curved coronary vessel, the arcuate member 60 may urge the device to self-orient within the curve such that the arcuate member 60 may be aligned with the vessel curve. It will be appreciated further that since the arcuate member 60 is located opposite to the exit port 50 of the device, the device may self-orient within the vessel curve such that the exit port 50 may be near the outer curve of the vessel. Referring again to FIG. 11, accordingly, the exit port 50 of the device may face the extravascular space 16 rather than the myocardium 10 when the arcuate member 60 is tracked through a curved section of a coronary vessel. Therefore, when the injection member 51 may be advanced from a retracted position to an extended position. The injection member 51 may penetrate the coronary vessel into the extravascular space.

Figure 12:
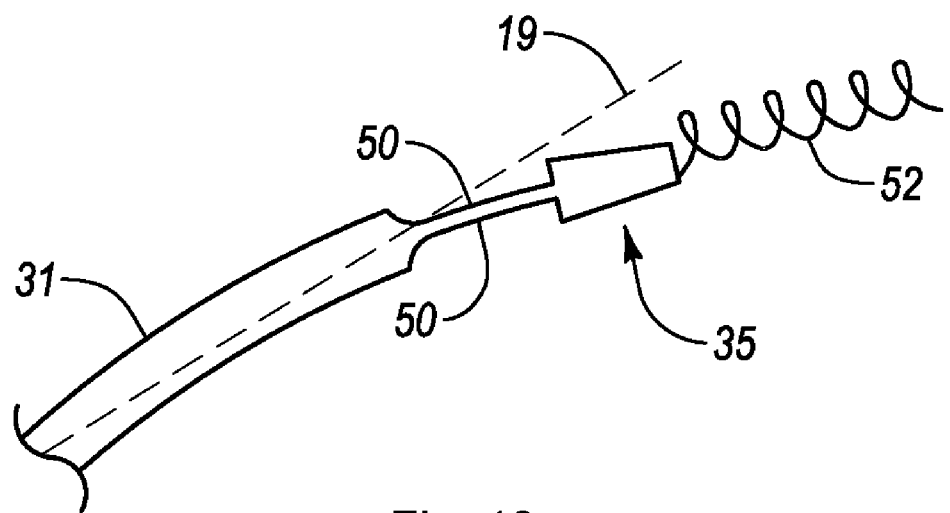
FIG. 12 is a perspective view of a distal end of a further configuration of a device in accordance with this disclosure, wherein the device has multiple exit ports.

Referring now to FIG. 12, a further configuration of a distal end 35 of a device for localized agent delivery is shown in accordance with the present disclosure. The instant configuration includes an elongated member 31 and a flexible tip 52. A plurality of exit ports 50 may be included within the elongated member 31, each exit port 50 may be adjacent to and/or spaced apart from the other.

The plural exit ports 50 may provide at least one device advantage. First, the reduction in cross-sectional material of elongated member 31 may produce a more flexible section, which may be capable of tracking through more tortuous anatomy. Also, the exit ports 50 may naturally align with the plane of the vessel curvature, potentially resulting in a self-orientation of at least one exit port 50 toward the extravascular space. Additionally, as the exit port 50 section of the device tracks through a vessel bend, the resulting curve in the device may cause the distal and proximal edges of at least one exit port 50 to separate even further. In combination with the self-orientation of the exit port 50, this may provide a larger port for the injection member 51 to be advanced through and/or directed along the tangential direction line 19.

Figure 13:
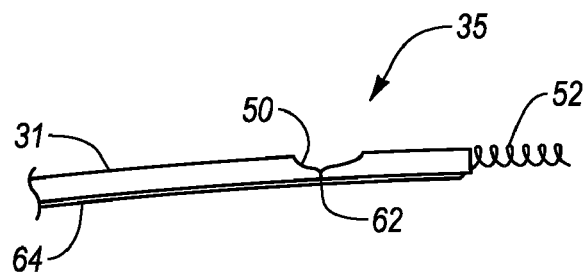
FIG. 13 is a side elevation view of a second end of a further configuration of a device in accordance with this disclosure, wherein an actuation cord is in a forward position.

Referring now to FIG. 13, a further configuration of a distal end 35 of a device for localized agent delivery is shown. The device includes an elongated member 31 and a flexible tip 52. Additionally, the elongated member 31 includes an exit port 50. An injection member 51 can be received within the elongated member 31 and be movable between a retracted and extended position through the exit port 50. A hinge element 62 may be disposed adjacent to the exit port 50. The hinge may be a separate element from the elongated member 31. For example, the elongated member 31 may have distal and proximal portions that are connected by a pin, which serves as a hinge. Alternatively, the hinge may be a living hinge. For instance, a reduced cross-sectional area portion of the elongated member 31 may have enough flexibility for the elongated member 31 to articulate back and forth, thus acting as a hinge.

Further still, the device may include an actuation member or cord 64 having a distal end 35 and a proximal end. The distal end 35 may be associated with the elongated member at a position distal to the exit port 50. The actuation member or cord 64 may have a low profile and/or may be constrained relative to the elongated member 31 over at least a portion of the device length.

Figure 14:
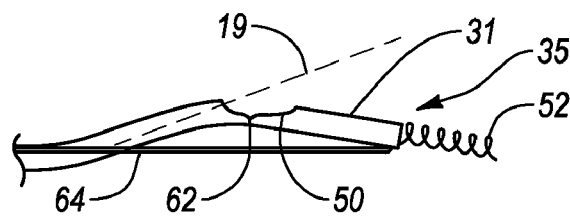
FIG. 14 is a side elevation view of a second end of a further configuration of a device in accordance with this disclosure, wherein an actuation cord is in tension.

Referring now to FIG. 14, in further accordance with this disclosure, a tensile load is applied to the actuation member or cord 64, thereby applying a moment arm to the elongated member 31 about the hinge. This may cause a strain in the elongated member 31 that may further widen the exit port 50. In addition, the resulting curve in the elongated member 31 may promote self-orientation of the exit port 50 toward the extravascular space, as previously described, due to the natural tendency of curvatures to align with each other. The combination of exit port 50 orientation and exit port 50 widening may permit easier advancement of the injection member 51, and/or may provide increased confidence that the injection member 51 will be directed toward the extravascular space along tangential direction line 19, when advanced.

Figure 15:
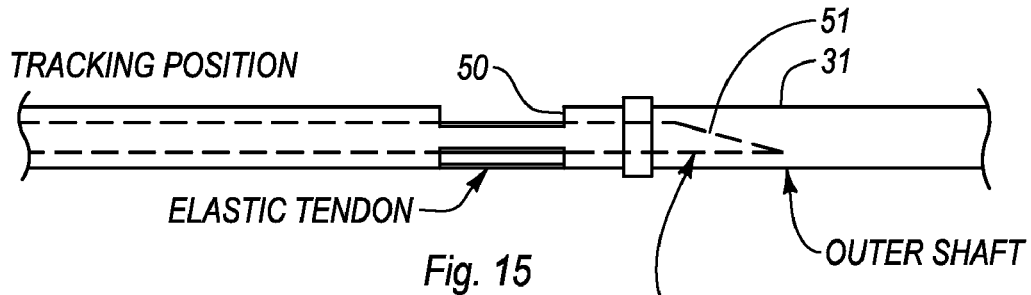
FIG. 15 is a side elevation view of a distal portion of a further configuration of a device in accordance with this disclosure.
Figure 16:
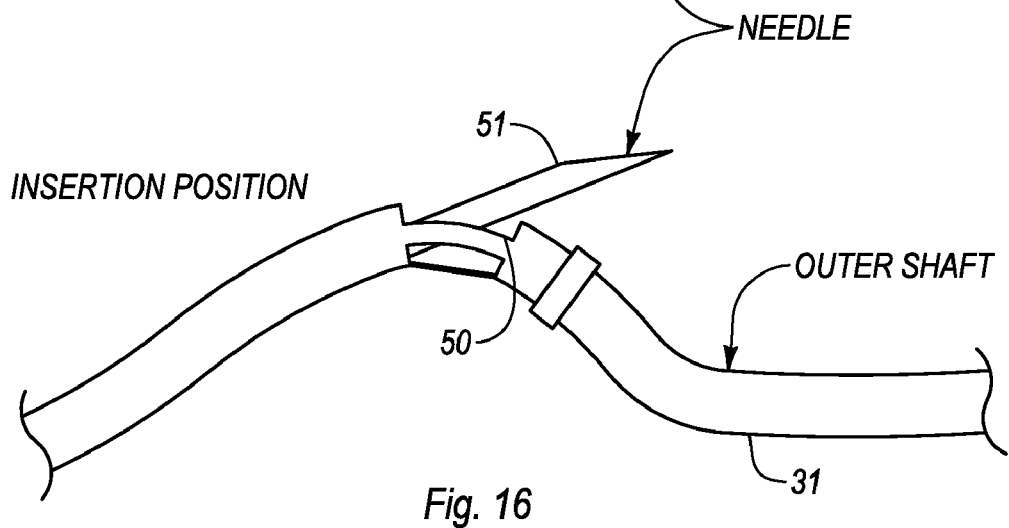
FIG. 16 is a side elevation view of a distal end of a further configuration of a device in accordance with this disclosure.

Referring now to FIGS. 15 and 16, a further configuration is shown. In this case, actuation member or cord 64 is constructed from an elastic material and associated with the elongated member 31 in a position distal and proximal to the exit port 50. The actuation member may provide a natural biasing moment upon the elongated member 31 about the hinge, as a result of its natural tendency to shorten in length.

As shown in FIG. 15, the tendency of the device to curve in the exit port section may initially be resisted by the advancement of an injection member 51 through the elongated member 31 distal to the exit port 50. The injection member 51 may provide sufficient resistance to the moment exacted upon the hinge by the actuation member or cord 64 to allow enough device structural rigidity to allow effective tracking through the anatomy to the treatment site without buckling. When the treatment site is reached, the injection member 51 may be retracted to a second position proximal to the exit port 50. In this second position, there may be reduced resistance to the moment caused by the actuation member or cord 64, and the device may be bent at the hinge section resulting in an overall curve of the device in that area and a tendency of the distal and proximal edges of the exit port 50 to separate further.

Referring now to FIG. 16, a third position of the injection member 51 is shown. The curvature of the device in the exit port section has resulted in self-orientation of the exit port 50 toward the extravascular space and has urged the exit port 50 to lengthen as described above. Therefore, advancement of the injection member 51 to the third position may ease and the injection member 51 may be directed toward the extravascular space.

A method for delivering a substance into the extravascular space is provided. The method may include several acts or steps performed in various orders, including the introduction of a device as embodied in the examples above, into the vascular system of a patient. For the purposes of understanding, it should be realized that the catheter might be tracked into a coronary vessel, including vessels that are arteries or veins. Although the device may be tracked to any point at which the extravascular space may be accessed through the vessel wall, it may be desirable to track the device to a distal region of the coronary vessel. This may ensure that the distal end 35 of the device is within a region of the coronary vessel with relatively low flow velocities and may reduce the risk of significant blood loss if the vessel is inadvertently dissected.

The device may be manipulated until the exit port 50 of the device self aligns with the outer radius of a vessel curve. The orientation may result from the tendency of a curve in the device to align with a curve of the vessel. The curve of the device may be due to a natural bias of the device, or the actuation of the device from a less curvaceous to a more curvaceous state, as explained above. Following alignment of the exit port 50, an injection member 51 may be advanced, penetrating the coronary vessel.

After penetrating the coronary vessel, the injection member 51 may be advanced far enough to ensure that the distal end 35 of the injection member 51 is within the extravascular space. A substance such as a therapeutic agent may then be injected through the injection member 51, into the extravascular space. The substance may disperse within the extravascular space by the natural mixing action of the heart 10 and the substance may be administered to the desired areas through this dispersion.

After delivering the substance, the injection member 51 may be removed into the coronary vessel entirely, through the vessel access site. Secondary acts or steps may be utilized to close the access site, if blood loss through the access site seems excessive. An example of a secondary step is the inflation of an angioplasty balloon within the access region to facilitate closure of the access site.

Figure 17:
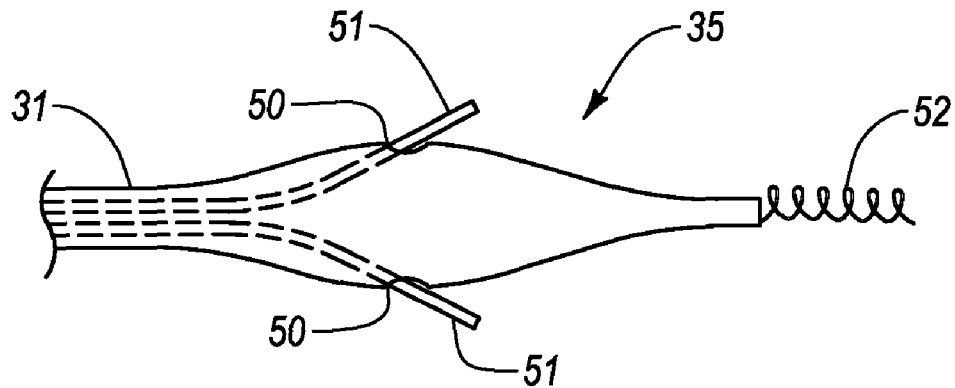
FIG. 17 is a side elevation view of a distal portion of a further configuration of a device in accordance with this disclosure, wherein an injection member is moveable in a substantially longitudinal direction.

Referring now to FIG. 17, a further configuration of a distal end 35 of a device for local agent delivery is shown. The device includes an elongated member 31 having a distal end 35 and a proximal end and further includes a flexible tip 52 disposed adjacent the distal end 35. The flexible tip 52 may improve the trackability of the device through an anatomy. At least one exit port 50 may be disposed within the elongated member 31 and may place an internal lumen of the elongated member 31 in fluid communication with the surrounding environment. At least one injection member 51 may be received within the internal lumen of the elongated member 31 and may be movable between a first retracted position and a second extended position, as shown. The injection member 51 may be configured and dimensioned to enable it to penetrate a coronary vessel wall 22 when advanced from the first toward the second position.

In one configuration, a plurality of injection members 51 may be disposed within the elongated member 31. As the plurality of injection members 51 are advanced to a second position, they may penetrate through the coronary vessel wall 22 at spaced access sites. At least one of these injection members 51 may be directed toward the extravascular space, permitting delivery of an agent thereto.

Figure 18:
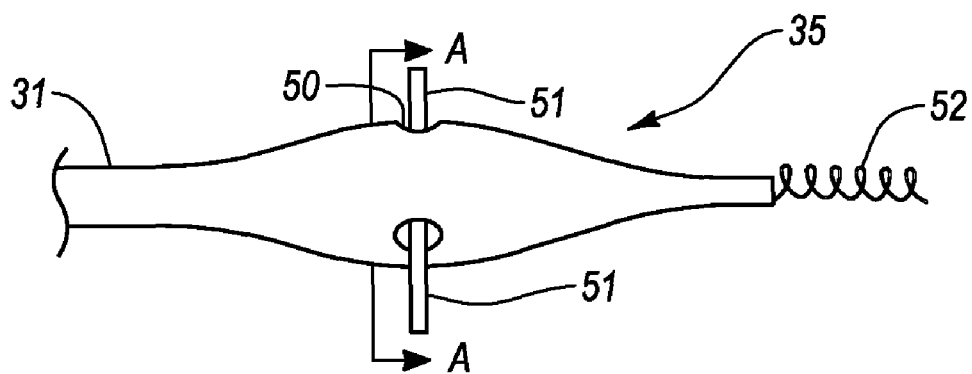
FIG. 18 is a side elevation view of a distal portion of a further configuration of a device in accordance with this disclosure, wherein an injection member is moveable in a substantially transverse direction.

Referring now to FIG. 18, a further configuration of a device is shown. The device includes injection members 51 that are configured to extend substantially in a transverse direction or plane when they are extended from a first retracted position to a second position.

Figure 19:
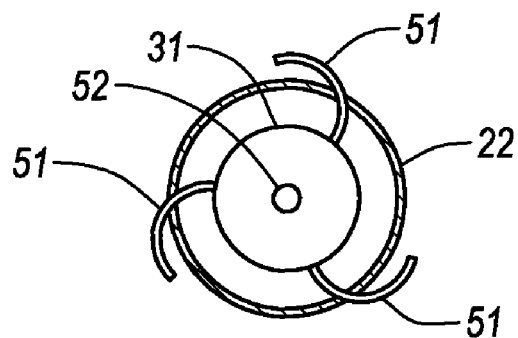
FIG. 19 is a cross sectional view illustrating a further configuration of a device in accordance with this disclosure, wherein an injection member is moveable in a substantially transverse direction, taken about line A-A of FIG. 18.

Accordingly, referring to FIG. 19, the injection member 51 may extend in a curvilinear fashion when viewed from an end of the device. It will be appreciated that the injection members 51 may initially extend in a direction that is substantially perpendicular to the coronary vessel wall 22, thereby facilitating penetration of the vessel wall, and may subsequently curve along a path that is substantially parallel to the coronary vessel wall 22. This subsequent direction may reduce the potential of penetrating the pericardial sac, since the potential contact angle between the injection member 51 and the pericardial sac, as well as the penetration depth, may be reduced.

A method for delivering a substance into the extravascular space is provided. The method may include several acts or steps performed in various orders, including the introduction of a device as embodied in the examples above, into the vascular system of a patient. For the purposes of understanding, it should be realized that the catheter might be tracked into a coronary vessel, including vessels that are arteries or veins. Although the device may be tracked to any point at which the extravascular space may be accessed through the vessel wall, it may be desirable to track the device to a distal region of the coronary vessel. This may ensure that the distal end 35 of the device is within a region of the coronary vessel with relatively low flow velocities and may reduce the risk of significant blood loss if the vessel is inadvertently dissected.

Once the device is positioned in the desired location, an injection member 51 may be advanced through the device exit ports 50, penetrating the coronary vessel. After penetrating the coronary vessel, an injection member 51 may be advanced far enough to ensure that the distal end 35 of the injection member 51 is within the extravascular space. A substance such as a therapeutic agent is may then be injected through the injection member 51, into the extravascular space. The substance may disperse within the extravascular space by the natural mixing action of the heart 10 and the substance may be administered to the desired areas through this dispersion.

After delivering the substance, the injection member 51 may be removed into the coronary vessel entirely, through the vessel access site. Secondary acts or steps may be utilized to close the penetration, if blood loss through the penetration seems excessive. An example of a secondary step is the inflation of an angioplasty balloon within the penetration region to facilitate closure of the penetration.

Figure 20:
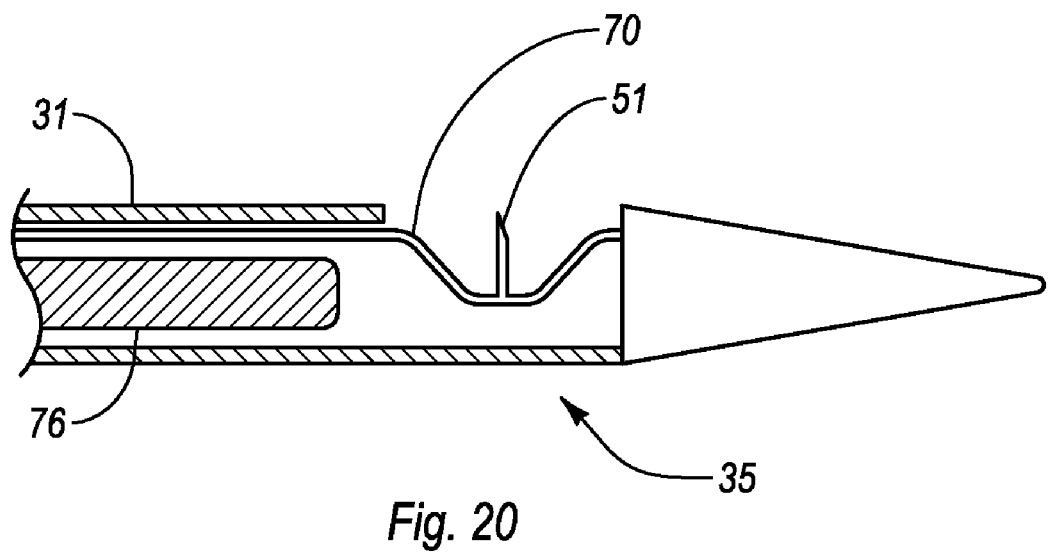
FIG. 20 is a side elevation view of a further configuration of a device in accordance with this disclosure illustrating an expandable structure in a low profile position.

Referring now to FIG. 20, a distal end 35 of a further configuration of a device for local agent delivery is shown. The device includes an elongated member 31 having a distal end 35 and a proximal end. An expandable section 70 may be positioned at or near the distal end 35 of the elongated member 31 and an injection member 51 may be associated with the expandable section 70. The device can further include an expansion actuation member 76 that can be moved between a first position and a second position. In the first position, the expandable section 70 may reside in a low profile configuration, making it easier for the device to be tracked through the anatomy.

Figure 21:
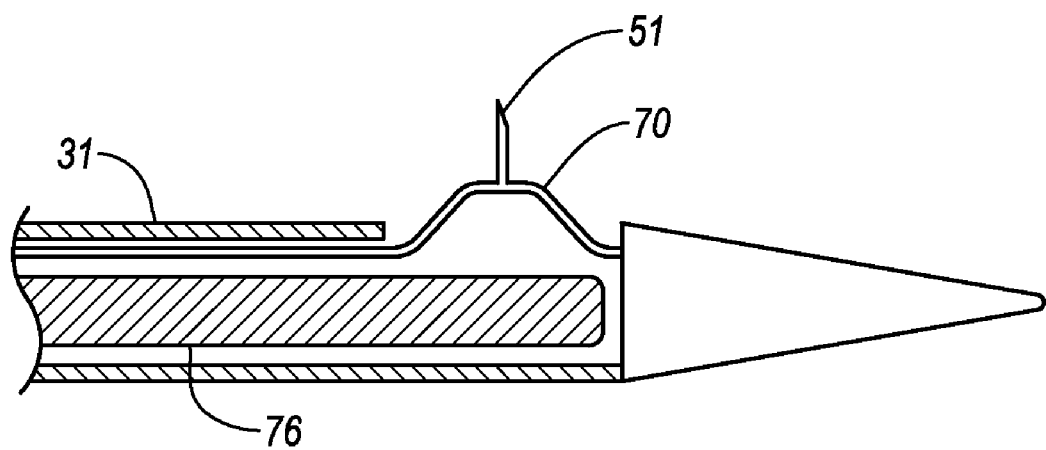
FIG. 21 is a side elevation view of a further configuration of a device in accordance with this disclosure illustrating an expandable structure in a high profile position.

Referring now to FIG. 21, by advancing the expansion actuation member 76 to a second position, the expandable section 70 may be contacted and/or urged toward an expanded configuration. This expansion may move the injection member 51 in a direction lateral to the elongated member 31 axis. When disposed within a coronary vessel, this can move the injection member 51 through the coronary vessel wall 22 and/or into the extravascular space.

In each of the preceding two configurations, the device is shown with a blunt distal end 35. It will be appreciated that these configurations may include a flexible tip 52 or a guidewire lumen for tracking over a guidewire 71, as previously disclosed and in accordance with the present disclosure.

A method for delivering a substance into the extravascular space is provided in accordance with the present disclosure. The method may include several acts or steps performed in various orders, including the introduction of a device as embodied in the examples above, into the vascular system of a patient. For the purposes of understanding, it should be realized that the catheter might be tracked into a coronary vessel, including vessels that are arteries or veins. Although the device may be tracked to any point at which the extravascular space may be accessed through the vessel wall, it may be desirable to track the device to a distal region of the coronary vessel. This may ensure that the distal end 35 of the device is within a region of the coronary vessel with relatively low flow velocities and may reduce the risk of significant blood loss if the vessel is inadvertently dissected.

Once the device is positioned in the desired location, an expandable section 70 of the device may be actuated, to bring an injection member 51 toward the coronary vessel wall. The injection member 51 may be advanced until it penetrates the coronary vessel.

After penetrating the coronary vessel, an injection member 51 may be advanced far enough to ensure that the distal end 35 of the injection member 51 is within the extravascular space. A substance such as a therapeutic agent may then be injected through the injection member 51, into the extravascular space. The substance may disperse within the extravascular space by the natural mixing action of the heart 10 and the substance may be administered to the desired areas through this dispersion.

After delivering the substance, the injection member 51 may be removed into the coronary vessel entirely, through the vessel access site. This may be facilitated by the retraction of the expandable section 70. Secondary acts or steps may be utilized to close the access site, if blood loss through the access site seems excessive. An example of a secondary act or step may include the inflation of an angioplasty balloon 72 within the access region to facilitate closure of the access site.

Figure 22:
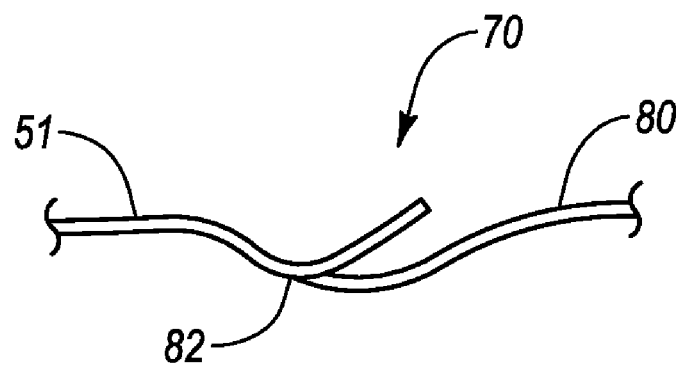
FIG. 22 is a side elevation view of a further configuration of an expandable section that can be incorporated within a device in accordance with this disclosure.

Referring now to FIG. 22, a further configuration of the expandable section 70 is shown. The expandable section 70 may include an injection member 51 and a composite member 80 associated with each other at a weld point 82. This configuration represents a further construction for the expandable section 70 that may offer a manufacturability advantage. The operation of the expandable section 70 may be controlled by the position of the expansion actuation member 76, as previously described.

Figure 23:
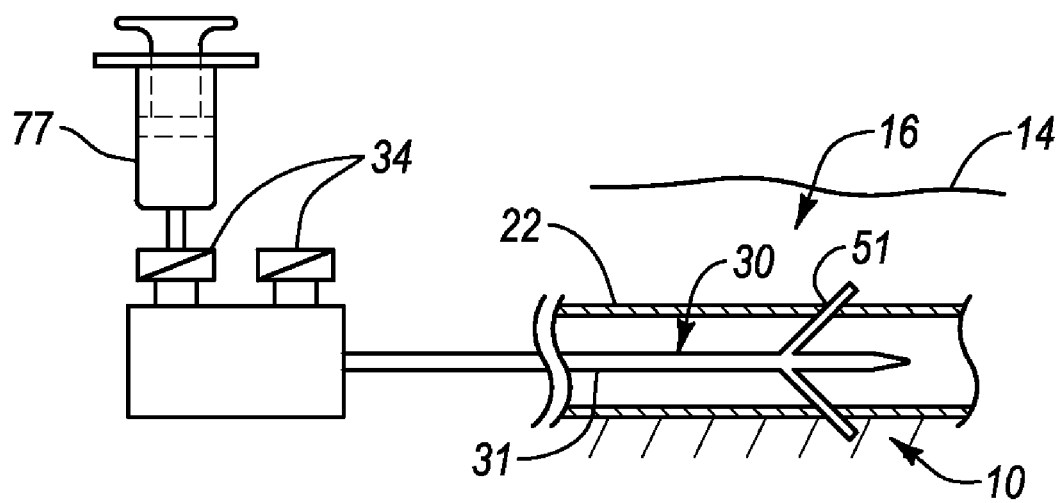
FIG. 23 is a side elevation view illustrating a system for delivering a therapeutic agent into the extravascular space through a device in accordance with this disclosure.

Referring now to FIG. 23, a further configuration of a device for localized agent delivery is shown. The device includes a plurality of injection members 51, shown here in a deployed configuration advanced through the coronary vessel wall 22. At least one injection member 51 may be inserted within the myocardium of the heart 10 and at least one injection may have accessed the extravascular space.

Further, the proximal end of each injection member 51 may be associated with a separate luer, thereby placing a syringe 77 in fluid communication with the injection lumen 36 disposed within the respective injection member 51. Therefore, if an agent is delivered through the luer of the injection member 51 disposed within the heart myocardium, then the agent may be delivered to the heart myocardium. Likewise, if an agent is delivered through the luer of the injection member 51 disposed within the extravascular space, then the agent may be delivered to the extravascular space.

Accordingly, after advancing the injection members 51 through the coronary vessel wall 22, contrast agent can be delivered from a syringe 77 through the luer to identify under fluoroscopy whether the respective injection member 51 is disposed within the extravascular space. A therapeutic agent can be delivered from a syringe 77 to the extravascular space, after, for example, the appropriate injection member 51 is identified using contrast agent.

In accordance with the present disclosure, an alternative method of identifying the injection member 51 location is provided. After advancing the injection members 51 through the coronary vessel wall 22, a vacuum may be applied to the luer. This may be accomplished through the use of a syringe 77, for example. If extravascular fluid is withdrawn into the syringe 77, then the respective injection member 51 is likely disposed within the extravascular space. Otherwise, it may be determined that the injection member 51 is probably not disposed within the extravascular space.

It will be understood that these methods of identifying the position of the injection members 51 relative to the extravascular space can apply to any of the configurations described above, in accordance with the present disclosure.

Figure 24:
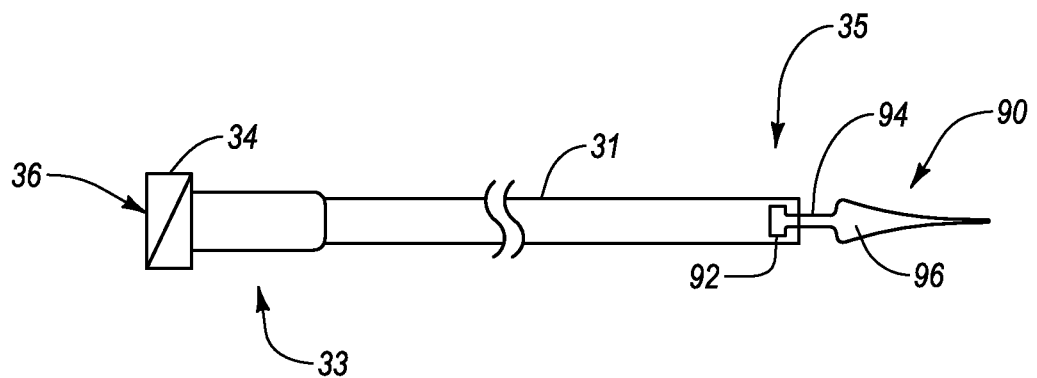
FIG. 24 is a side elevation view of a further configuration of a device in accordance with this disclosure having a detachable access tip.

Referring now to FIG. 24, a further configuration of a device for localized agent delivery is shown. The device includes an elongated member 31 having a distal end 35 and a proximal end. An injection lumen 36 is disposed therebetween. A luer may be associated with the proximal end 33 of the elongated member 31 and may permit the attachment of a syringe 77 and/or communication of an agent through injection lumen 36.

In this configuration, a detachable tip 90 may be associated with the distal end 35 of the elongated member 31. The detachable tip 90 may include several elements that may contribute to the structure and function of the component. A head 92 may be disposed near the proximal end of the detachable tip 90. The head 92 may be configured and dimensioned to fit within the injection lumen 36 and may include a proximal surface that can be acted upon by a fluid delivered through the injection lumen 36. The head 92 may have a distal surface that may act to affect the distal movement of the removable tip through tissue.

A shank 94 may be associated with the head 92 and/or with a tooth element 96. The tooth 96 may be disposed at or near the distal end of the detachable tip 90. It may include a cross-sectional area that may reduce in the distal direction. This may permit the distal region of the tooth 96 to penetrate tissue with relative ease. As the tooth 96 is advanced through tissue, the tissue may be distended around the tooth surface. After the proximal end of the tooth 96 has been inserted through tissue, the tissue may recoil toward the profile of the shank 94. In this way, an area of tissue may act upon a proximal end of the tooth 96 to resist movement of the detachable tip 90 in a proximal direction. In cooperation, the elements of the detachable tip 90 may promote retention of the component within tissue.

Figure 25:
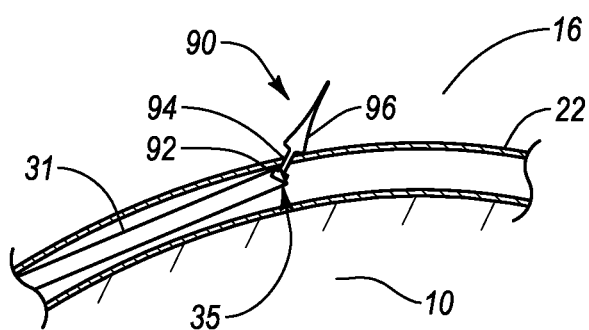
FIG. 25 is a perspective view of a further configuration of a device in accordance with this disclosure having a detachable access tip and disposed within a coronary vessel.

Referring now to FIG. 25, in one configuration, the elongated member 31 may be advanced through the coronary anatomy until the distal end 35 is within a vessel bend. As discussed previously, the vessel bend may urge the distal end 35 toward the greater curve of the vessel. As the elongated member 31 is advanced further, the distal end of the tooth 96 may penetrate the coronary vessel wall 22, entering into the extravascular space. The device can be advanced until the external surface of the coronary vessel wall 22 is proximal to the tooth 96.

Detachment of the tip can be accomplished in several ways. In one configuration, the device can be retracted. The retention force placed on the proximal end 33 of the tooth 96 by the coronary vessel wall 22 may be greater than the retention force applied to the head 92 by the injection lumen 36. This may result in the tip detaching within the coronary vasculature, with the tooth 96 substantially disposed within the extravascular space.

Further, a fluid such as saline or contrast agent can be delivered through the injection lumen 36. The fluid pressure may act upon the proximal surface of the head, urging the tip to detach from the elongated member 31.

In another configuration, the detachable tip 90 may be formed from a bioabsorbable material. This material could be poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyanhydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, combinations thereof, chitosan, PBT, 4-hydroxybutyrate, 3-hydroxybutyrate, or PEG, to name only a few. Further still, a therapeutic agent may be integrally formed within the detachable tip 90 structure. Further, a therapeutic agent may be applied to a surface of the detachable tip 90 in the form of a coating, for example. Accordingly, after the tip 90 is disposed within the coronary vasculature, it may begin to degrade, thereby releasing therapeutic agent into the extravascular space.

An advantage of this configuration may include that the access site 20 in the coronary vessel wall 22 will likely naturally heal and close as the detachable tip 90 degrades within the body. This may reduce the need for subsequent closure techniques after removing the device from the anatomy.

A method for delivering a substance into the extravascular space is provided. The method may include several acts or steps performed in various orders, including the introduction of a device as embodied in the examples above, into the vascular system of a patient. For the purposes of understanding, it should be realized that the catheter may be tracked into a coronary vessel, including vessels that are arteries or veins. Although the device may be tracked to any point at which the extravascular space may be accessed through the vessel wall, it may be desirable to track the device to a distal region of the coronary vessel. This may ensure that the distal end 35 of the device is within a region of the coronary vessel with relatively low flow velocities and may reduce the risk of significant blood loss if the vessel is inadvertently dissected.

The device may be advanced until the detachable tip 90 has penetrated the coronary vessel. This may be facilitated by tracking the device through a coronary vessel with a given curvature.

After penetrating the coronary vessel, the tip 90 may become detached, remaining in communication with the extravascular space. The detachable tip 90 may degrade, releasing a substance that may disperse within the extravascular space by the natural mixing action of the heart 10 and the substance may be administered to the desired areas through this dispersion. After delivering the detachable tip 90, the device body may be removed from the coronary vessel.

Figure 26:
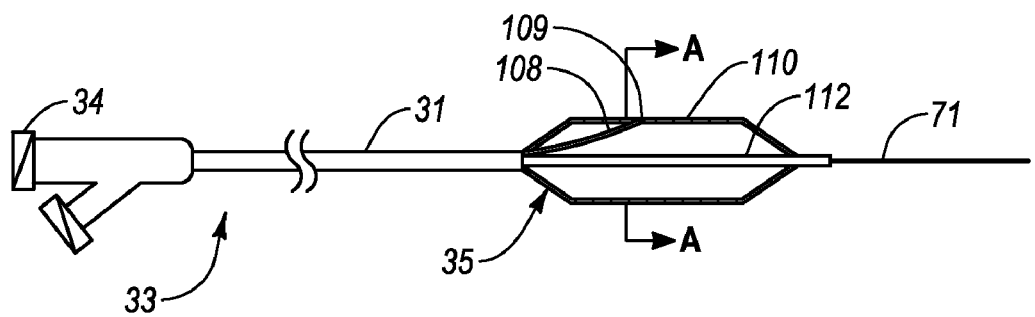
FIG. 26 is a side elevation view of a further configuration of a device in accordance with this disclosure having a fluid injection lumen.

Referring now to FIG. 26, an alternative configuration of a device for localized agent delivery is shown having a fluid injection feature. The fluid injection lumen 108 has a proximal end 33 and a distal end 35, with an injection port 109 that may be disposed adjacent the distal end 35. The device includes an elongated member 31 having a proximal end 33 and a distal end 35. A luer fitting 34 may be associated with the proximal end 33. The luer fitting 34 may include at least two separate luer channels (not shown). At least one luer channel may be in communication with the fluid injection lumen 108. At least one luer channel is in communication with an inflation lumen (not shown) defined between the elongated member 31 and a guidewire lumen 112 disposed within the elongated member 31. The guidewire lumen 112 may be configured and dimensioned to receive a guidewire 71 thereby permitting the device to be tracked over a guidewire 71 disposed within a vascular anatomy. The device may include an expandable structure 110 that may be disposed at or near the distal end 35 of the device and/or may be placed in fluid communication with the inflation lumen. The expandable structure 110 may include a single balloon element or multiple balloon elements. The injection port 109 may be further disposed adjacent the surface of the balloon structure.

Figure 27:
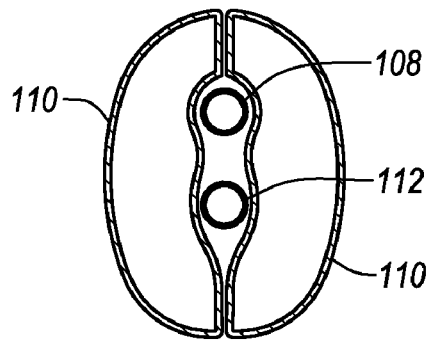
FIG. 27 is a cross-sectional view of a working region of a device in accordance with this disclosure having a fluid injection lumen, taken about line A-A of FIG. 26.

Referring now to FIG. 27, the expandable structure 110 may be formed from two or more separate balloon elements, although it may also be formed from a single balloon element. In this configuration, each balloon element may be formed in a substantial "D" shape during the balloon forming process, although other configurations are possible. For instance, two balloons with circular cross-sections can be constrained by a tubular sheath, urging them toward a substantially "D" shaped configuration. The balloon elements can be positioned on opposite sides of the fluid injection lumen 108 and the guidewire lumen 112 in order to maintain a balanced profile and to ease deliverability of the device through the coronary anatomy.

The expandable structure 110 may be formed from an expandable metallic or plastic structure, such as a self-expanding nitinol scaffold. This type of structure would permit maintained blood flow within the vessel even during expansion. It may be desirable to include a sheath component around the expandable structure 110 in order to separate the vessel wall from the blood flow, potentially providing an advantage that will be explained in greater detail below.

Figure 28:
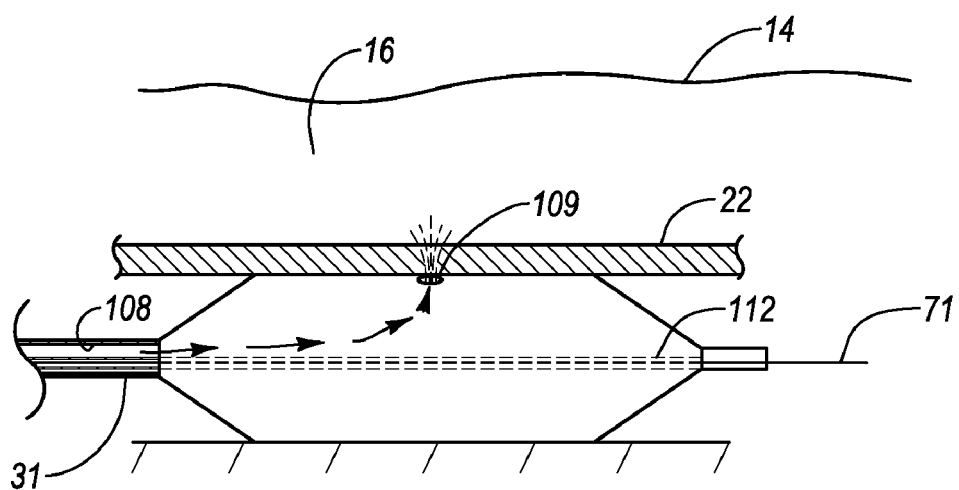
FIG. 28 is a perspective view of a further configuration of a device in accordance with this disclosure having a fluid injection lumen being disposed within a coronary vessel.

Referring now to FIG. 28, a further configuration of the device having a fluid injection feature is shown. In this configuration, the device does not include a fluid injection lumen 108. Fluid may be delivered through the inflation lumen into the balloon element. Fluid may ejected through the fluid injection port 109 formed in the surface of the balloon element.

A method is provided for delivering an agent into the extravascular space using a device with an injection port 109. A guidewire 71 may be tracked through the coronary anatomy, such as to a distal vessel location. The device may be tracked over the guidewire 71 until the balloon structure is adjacent the desired treatment location. A fluid source may be attached to the luer fitting 34 (FIG. 30) and pressurized fluid may be delivered through the inflation lumen of the device, causing the balloon structure to expand against the coronary vessel wall 22. This may bring the injection port 109 into close proximity with the coronary vessel wall 22. An agent source such as a syringe 77 may be attached to the luer fitting 34, and agent may be delivered under pressure through the injection port 109. As described previously, this can be accomplished with or without the use of a fluid injection lumen 108, depending upon the configuration of the device. The agent may be delivered at a sufficient velocity to eject through the injection port 109 and/or to penetrate through the coronary vessel wall 22 into the extravascular space.

With this configuration, the fluid jet could permit the coronary vessel to recoil to a substantially closed position after agent injection. Additionally, the expandable structure 110 can remain expanded after fluid injection, permitting a chance for the vessel to heal adequately before re-establishing blood flow within the coronary vessel. As a result, this configuration may reduce the potential of excessive bleeding into the extravascular space.

Referring now to FIG. 29, a further configuration of a device for local agent delivery is provided. The device includes a stent structure 120 with at least one strut element 122. A series of strut elements 122 can be arranged in circumferentially expandable rings. The stent structure 120 includes at least one protrusion 124 associated with a stent strut and which extends from the stent strut. As shown, the at least one protrusion 124 is formed in a direction that is substantially parallel to the direction of stent expansion. It will be understood, however, that the protrusion 124 can extend from the stent strut at any angular orientation relative to the stent strut in accordance with this disclosure. The angular orientation may be such that it may allow the protrusion to engage with the tissue.

Referring now to FIG. 30 and FIG. 31, a further configuration is shown. The protrusions 124 are formed in a direction that is substantially tangential to the stent circumference. This may allow the protrusions to embed within the coronary vessel wall 22 to a shallower depth while maintaining the same volume to surface area ratio for the protrusions 124.

The stent structure 120 of this configuration can be formed from a metal such as stainless steel, cobalt-chromium, MP35N, or Nitinol. It may also be formed from a plastic such as nylon, or a bioabsorbable material such as poly-L-lactide, polyester amide, iron-silicon composite, or any other metallic or polymeric bioabsorbable material. A number of other materials and methods for fabricating the stent may be used.

In accordance with this disclosure, a therapeutic agent may be integrally formed within the protrusions 124. In another example, a therapeutic agent may be subsequently added as a surface coating, for example.

After deploying the stent by, for example, releasing a self-expanding stent to allow it to expand or inflating a balloon to expand a balloon expandable stent, the protrusions 124 may penetrate the coronary vessel wall 22. Therapeutic agent may subsequently be released into the extravascular space. This release may occur as a result of degradation of protrusions 124 in the case of bioabsorbable protrusions, or due to the surface release of therapeutic agent in the case of surface coated protrusions, or for other reasons.

This configuration may eliminate the need to close the access site within the coronary vessel, since the stent structure 120 itself may seal off the penetration, thereby preventing excessive bleeding into the extravascular space.

In accordance with each of the configurations disclosed above, it may be desirable to promote healing of a access site in the coronary vessel wall 22 after and/or during removal of the device into the coronary vessel. A method of promoting healing of a vessel access site can be provided that includes application of a vasoconstrictor through a device lumen adjacent to the access site. The vasoconstrictor may be alcohol, for example, or any other agent suitable for urging the vessel to close the access site.

Pressure can be applied to the access site after removing the device into the coronary vessel. This can be accomplished in a number of ways. In one example, a balloon may be inflated within the coronary vessel adjacent to the access site. The balloon surface may contact the vessel penetrate, providing pressure to the vessel area and/or promoting closure of the access site.

In an alternative configuration, an expandable structure 110 such as a Nitinol stent may include a sheath disposed about an external surface of the stent. The expandable structure 110 may thus be deployed adjacent to the vessel access site, thereby contacting the vessel access site and applying pressure to the vessel area and/or promoting closure of the access site.

In many of these configurations, the device is used to deliver an agent, such as a therapeutic agent, into the extravascular space in order to treat vascular diseases. It should be appreciated that the devices may serve alternative purposes. For example, the devices could be used to deliver substances into the myocardium of the heart 10. This can be beneficial, for example, in the delivery of cells to ischemic heart tissue, fostering cell therapy of the damaged tissue. Also, devices in accordance with the embodiments described above could be used to deliver agents into other patient tissues or spaces that surround bodily lumens. For example, such devices may be used to penetrate through a urethra in order to deliver an agent into a prostate gland. Further, such devices could access the liver through the walls of a hepatic vein. These examples are intended to show the breadth of applications that there are for a device in accordance with this disclosure. It will therefore be appreciated that the embodiments disclosed above are not intended to limit the disclosure to any one application, but should instead be regarded as illustrative of the disclosure and its advantages.

It will be further understood that the present disclosure encompasses many configurations. These configurations may be useful alone or in combination. The above disclosure is intended to be illustrative and not exhaustive. This description will suggest many variations and alternatives to one of ordinary skill in this art. All of these alternatives and variations are intended to be included within the scope of the attached claims. Those familiar with the art may recognize other equivalents to the specific configurations described herein which equivalents are also intended to be encompassed by the claims attached hereto.

While the present disclosure is described herein in terms of certain configurations or embodiments, various modifications and improvements may be made to the disclosure without departing from the scope thereof. Moreover, although individual features of one configuration or embodiment of the disclosure may be discussed herein or shown in the drawings of the one configuration or embodiment and not in other configurations or embodiments, it should be apparent that individual features of one configuration or embodiment may be combined with one or more features of another configuration or embodiment or features from a plurality of configurations or embodiments of the disclosure.

The present disclosure, therefore, may be embodied in other specific forms without departing from its spirit or essential characteristics. The described configurations are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device for localized agent delivery through the wall of a coronary vessel, comprising:
    an elongated member having a first end and a second end, wherein the elongated member is more flexible near the second end than near the first end;
    a longitudinal axis defined between the first and second end;
    at least one lumen substantially aligned with the longitudinal axis between the first end and the second end of the elongated member;
    a side exit port disposed proximal from the second end of the elongated member, the side exit port communicating with the at least one lumen and the elongated member being configured to preferentially bend at the side exit port;
    a second side exit port disposed opposite the first side exit port, whereby the flexibility of the elongated member near the side exit ports is increased and at least one of the side exit ports is biased toward the outer curve when the device is placed in a bend;
    at least one injection member disposed within the at least one lumen having a proximal end and a distal end, the distal end being movable from a first position within the at least one lumen to a second position through the first side exit port, the injection member further comprising an injection lumen placing the proximal and distal end in fluid communication; and
    a substantially arcuate member disposed along the elongated member near the side exit port, the arcuate member being configured to bias the elongated member toward a curved configuration.

2. The device of claim 1, further comprising an actuation cord radially constrained along the elongated member, being substantially misaligned with the side exit port and having a proximal end and a distal end, the distal end associated with the elongated member distal to the side exit port, whereby when a tensile load is placed on the actuation cord the elongated member is biased toward a curved configuration.

3. A device for localized agent delivery through the wall of a coronary vessel, comprising:
    an elongated member having a first end and a second end, wherein the elongated member is more flexible near the second end than near the first end;
    a longitudinal axis defined between the first and second end;
    at least one lumen substantially aligned with the longitudinal axis between the first end of the elongated member and a first side exit port disposed proximal from the second end of the elongated member and distal from the first end of the elongate member, the first side exit port communicating with the at least one lumen and the elongated member being configured to preferentially bend at the first side exit port, the elongated member comprising a second exit port disposed opposite the first exit port, whereby the flexibility of the elongated member near the exit ports is increased and at least one of the exit ports is biased toward the outer curve when the device is placed in a bend; and
    at least one injection member disposed within the at least one lumen having a proximal end and a distal end, the distal end being movable from a first position within the at least one lumen to a second position through the first exit port, the injection member further comprising an injection lumen placing the proximal and distal end in fluid communication.

4. The device of claim 3, further comprising a substantially arcuate member disposed along an exterior of the elongated member near the first side exit port, the exteriorly mounted arcuate member being configured to bias the elongate member to a curved configuration.

5. The device of claim 4, wherein the arcuate member comprises a curved metal band or a curved plastic band.

6. The device of claim 3, further comprising a flexible tip extending from the elongated member distal end.

7. The device of claim 3, wherein the at least one injection member is disposable within a portion of the at least one lumen distal the first side exit port.

8. A device for localized agent delivery through the wall of a coronary vessel, comprising:
    an elongated member having a first end, a second end, and a flexible tip extending from the second end, wherein the elongated member is more flexible near the second end than near the first end;

a longitudinal axis defined between the first and second end;

at least one lumen substantially aligned with the longitudinal axis between the first end of the elongated member and a side exit port disposed proximal from the second end of the elongated member and distal from the first end of the elongate member, the side exit port having a proximal edge and a distal edge and communicating with the at least one lumen, the elongated member being configured to preferentially bend at the side exit port and separate the proximal edge from the distal edge;

an exterior actuation cord having a proximal end and a distal end, the distal end coupled to an exterior portion of the elongated member distal to the side exit port, the elongated member further comprises a hinge disposed at the side exit port, the hinge being movable when the tensile load is placed on the actuation cord; and at least one injection member disposed within the at least one lumen having a proximal end and a distal end, the distal end being movable from a first position within the at least one lumen to a second position through the side exit port, the injection member further comprising an injection lumen placing the proximal and distal end in fluid communication.

9. The device of claim 8, further comprising a substantially arcuate member disposed along a portion of an exterior of the elongated member about the side exit port, the exteriorly mounted arcuate member being configured to bias the elongate member to a curved configuration.

10. The device of claim 9, wherein the arcuate member comprises a deformable curved metal band or a shape-memory curved metal band.

11. The device of claim 8, further comprising a second side exit port disposed opposite the first side exit port, whereby the flexibility of the elongated member near the side exit ports is increased and at least one of the side exit ports is biased toward the outer curve when the device is placed in a bend.

12. A device for localized agent delivery through the wall of a coronary vessel, comprising:

an elongated member having a first end and a second end, wherein the elongated member is more flexible near the second end than near the first end;

a longitudinal axis defined between the first and second end;

at least one lumen substantially aligned with the longitudinal axis between the first end of the elongated member and a side exit port disposed proximal from the second end of the elongated member and distal from the first end of the elongate member, the side exit port communicating with the at least one lumen and the elongated member being configured to preferentially bend at the side exit port;

at least one injection member disposed within the at least one lumen having a proximal end and a distal end, the distal end being movable from a first position within the at least one lumen to a second position through the side exit port, the injection member further comprising an injection lumen placing the proximal and distal end in fluid communication;

an actuation cord having a proximal end and a distal end, the distal end coupled to an exterior portion of the elongated member distal to the exit port, wherein when a tensile load is placed on the actuation cord the elongated member is biased toward a curved configuration; and a living hinge disposed at the side exit port, the living hinge being movable when the tensile load is placed on the actuation cord.

13. The device of claim 12, further comprising a flexible tip extending from the elongated member distal end.

14. The device of claim 12, wherein the at least one injection member is disposable within a portion of the at least one lumen distal the side exit port.

15. A device for localized agent delivery through the wall of a coronary vessel, comprising:

an elongated member having a first end, a second end, and a flexible tip extending from the second end, a side exit port and a second side exit port disposed opposite the side exit port, wherein the elongated member is more flexible near the second end than near the first end;

a longitudinal axis defined between the first and second end;

at least one lumen substantially aligned with the longitudinal axis between the first end of the elongated member and the side exit port disposed proximal from the second end of the elongated member and distal from the first end of the elongate member, the side exit port having a proximal edge and a distal edge and communicating with the at least one lumen, the elongated member being configured to preferentially bend at the side exit port and separate the proximal edge from the distal edge, whereby the flexibility of the elongated member near the side exit ports is increased and at least one of the side exit ports is biased toward the outer curve when the device is placed in a bend; and at least one injection member disposed within the at least one lumen having a proximal end and a distal end, the distal end being movable from a first position within the at least one lumen to a second position through the side exit port, the injection member further comprising an injection lumen placing the proximal and distal end in fluid communication.

16. The device of claim 15, further comprising a substantially arcuate member disposed along a portion of an exterior of the elongated member about the side exit port, the exteriorly mounted arcuate member being configured to bias the elongate member to a curved configuration.

17. The device of claim 16, wherein the arcuate member comprises a deformable curved metal band or a shape-memory curved metal band.

* * * * *